United States Patent
Nie et al.

(10) Patent No.: US 12,159,694 B2
(45) Date of Patent: Dec. 3, 2024

(54) SYSTEM AND METHOD FOR RETRIEVAL-BASED CONTROLLABLE MOLECULE GENERATION

(71) Applicant: NVIDIA Corporation, Santa Clara, CA (US)

(72) Inventors: Weili Nie, Sunnyvale, CA (US); Zichao Wang, Burlingame, CA (US); Chaowei Xiao, Seattle, WA (US); Animashree Anandkumar, Pasadena, CA (US)

(73) Assignee: NVIDIA Corporation, Santa Clara, CA (US)

( * ) Notice: Subject to any disclaimer, the term of this patent is extended or adjusted under 35 U.S.C. 154(b) by 0 days.

(21) Appl. No.: 18/353,773

(22) Filed: Jul. 17, 2023

(65) Prior Publication Data

US 2024/0029836 A1    Jan. 25, 2024

Related U.S. Application Data

(60) Provisional application No. 63/389,728, filed on Jul. 15, 2022.

(51) Int. Cl.
*G16C 20/00* (2019.01)
*G06N 5/04* (2023.01)
(Continued)

(52) U.S. Cl.
CPC ............... *G16C 20/90* (2019.02); *G06N 5/04* (2013.01); *G06N 7/01* (2023.01); *G06N 20/00* (2019.01);
(Continued)

(58) Field of Classification Search
CPC ........ G16C 20/90; G16C 20/70; G16C 20/10; G16C 20/30; G06N 20/00; G06N 20/10; G06N 7/01; G06F 30/10
See application file for complete search history.

(56) References Cited

U.S. PATENT DOCUMENTS

2019/0286792 A1 * 9/2019 Li ............................ G06N 5/04
2021/0271980 A1 * 9/2021 Polykovskiy .......... G06N 3/088
(Continued)

FOREIGN PATENT DOCUMENTS

WO    WO 2020243440 A1 * 12/2020
WO    WO 2021229454 A1 * 11/2021

OTHER PUBLICATIONS

Sliwoski, G., et al., "Computational methods in drug discovery," Pharmacological Reviews, 66(1):334-395, Dec. 2013.
(Continued)

*Primary Examiner* — Srirama Channavajjala
(74) *Attorney, Agent, or Firm* — Leydig, Voit & Mayer, Ltd.

(57) ABSTRACT

A machine learning framework is described for performing generation of candidate molecules for, e.g., drug discovery or other applications. The framework utilizes a pre-trained encoder-decoder model to interface between representations of molecules and embeddings for those molecules in a latent space. A fusion module is located between the encoder and decoder and is used to fuse an embedding for an input molecule with embeddings for one or more exemplary molecules selected from a database that is constructed according to a design criteria. The fused embedding is decoded using the decoder to generate a candidate molecule. The fusion module is trained to reconstruct a nearest neighbor to the input molecule from the database based on the sample of exemplary molecules. An iterative approach may be used during inference to dynamically update the database to include newly generated candidate molecules.

19 Claims, 8 Drawing Sheets

(51) Int. Cl.
| | |
|---|---|
| G06N 7/01 | (2023.01) |
| G06N 20/00 | (2019.01) |
| G06N 20/10 | (2019.01) |
| G16C 20/10 | (2019.01) |
| G16C 20/30 | (2019.01) |
| G16C 20/70 | (2019.01) |
| G16C 20/90 | (2019.01) |

(52) U.S. Cl.
CPC ............ *G06N 20/10* (2019.01); *G16C 20/10* (2019.02); *G16C 20/30* (2019.02); *G16C 20/70* (2019.02)

(56) References Cited

U.S. PATENT DOCUMENTS

| | | | | |
|---|---|---|---|---|
| 2021/0313016 | A1* | 10/2021 | Jones | G06N 20/10 |
| 2022/0198286 | A1* | 6/2022 | Prat | G06V 10/82 |
| 2022/0270713 | A1* | 8/2022 | Spagnoli | G16C 20/30 |
| 2023/0245003 | A1* | 8/2023 | Hummelshøj | G06N 7/01 706/12 |
| 2023/0315924 | A1* | 10/2023 | Hummelshøj | G06F 30/10 703/1 |

OTHER PUBLICATIONS

Jensen, I.H., "A graph-based genetic algorithm and generative model/monte carlo tree search for the exploration of chemical space," Chemical Science, 10(12):3567-3572, 2019.
Yoshikawa, N., et al.,, "Population-based de novo molecule generation, using grammatical evolution," Chemistry Letters, 47(11): 1431-1434, Nov. 2018.
Hoffman, S.C., et al., "Optimizing molecules using efficient queries from property evaluations," Nature Machine Intelligence, 4(1):21-31, Dec. 2021.
Tang, B., et al., "Generative AI models for drug discovery," In Biophysical and Computational Tools in Drug Discovery, pp. 221-243, Springer International Publishing, 2021.
Chen, H., "Can generative-model-based drug design become a new normal in drug discovery?" Journal of Medicinal Chemistry, 65(1):100-102, Dec. 2021.
Zhou, Z., et al., "Optimization of molecules via deep reinforcement learning," Scientific Reports, 9(1), Jul. 2019.
Popova, M., et al., "Deep reinforcement learning for de novo drug design," Science Advances, 4(7), Jul. 2018.
Olivecrona, M., et al., "Molecular de-novo design through deep reinforcement learning," Journal of Cheminformatics, 9(1), Sep. 2017.
Jin, V., et al., "Multi-objective molecule generation using interpretable substructures," In Hal Daume III and Aarti Singh, editors, Proceedings of the 37th International Conference on Machine Learning, vol. 119 of Proceedings of Machine Learning and Research, pp. 4849-4859, PMLR, 13-18, Jul. 2020.
Brown, N., et al., "GuacaMol: Benchmarking models for de novo molecular design," Journal of Chemical Information and Modeling, 59(3): 1096-1108, Mar. 2019.
Lim, J., et al., "Molecular generative model based on conditional variational autoencoder for de novo molecular design," Journal of Cheminformatics, 10(1), Jul. 2018.
Shin, B., et al., "Controlled molecule generator for optimizing multiple chemical properties," In Proceedings of the Conference on Health, Inference, and Learning, ACM, Apr. 2021.
Winter, R., et al., "Efficient multi-objective molecular optimization in a continuous latent space," Chemical Science, 10(34):8016-8024, 2019.
Das, P., et al., "Accelerated antimicrobial discovery via deep generative models and molecular dynamics simulations," Nature Biomedical Engineering, 5(6):613-623, Mar. 2021.
Dalke, A., et al., "mmpdg: An open-source matched molecular pair platform for large multiproperty data sets," Journal of Chemical Information and Modeling, 58(5):902-910, May 2018.
Jin, W., et al., "Junction tree variational autoencoder for molecular graph generation," In Jennifer Dy and Andreas Krause, editors, Proceedings of the 35th International Conference on Machine Learning, vol. 80 of Proceedings of Machine Learning and Research, pp. 2323-2332, PMLR, 10-15, Jul. 2018.
You, J., et al., "Graph convolutional policy network for goal-directed molecular graph generation," In Proceedings of the 32nd International Conference on Neural Information Processing Systems, NIPS 2018, pp. 6412-6422, Red Hook, NY, Curran Associates, Inc.
Bahdanau, D., et al., "Neural machine translation by jointly learning to align and translate," In Yoshua Bengio and Yann LeCun, editors, 3rd International Conference on Learning Representations, ICLR 2015, San Diego, Ca, USA, May 7-9, 2015, Conference Track Proceedings, 2015.
Jin, W., et al., "Learning multimodal graph-to-graph translation for molecule optimization," In International Conference on Learning Representations 2019.
Jin, W., et al., "Hierarchical Graph-to-Graph Translations for Molecules," arXiv preprint, arXiv:1907.11223, Jun. 2019.
Maragakis, P., et al., "A deep-learning view of chemical space designed to facilitate drug discovery," Journal of Chemical Information and Modeling, 60(10):4487-4496, Jul. 2020.
Nigam, A., et al., "Augmenting Genetic Algorithms with Deep Neural Networks for Exploring the Chemical Space," arXiv preprint, arXiv:1909.11655, Sep. 2019.
Rao, R., et al., "MSA Transformer," In Proceedings of the 38th International Conference on Machine Learning, vol. 139 of Proceedings of Machine Learning Research, pp. 8844-8856, PMLR, 18-24, Jul. 2021.

\* cited by examiner

SYSTEM AND METHOD FOR RETRIEVAL-BASED CONTROLLABLE MOLECULE GENERATION

CROSS-REFERENCE TO RELATED APPLICATIONS

This application claims priority to U.S. Provisional Patent Application No. 63/389,728, filed on Jul. 15, 2022, which is hereby incorporated by reference in its entirety.

BACKGROUND

Generating new molecules with specified chemical and biological properties via generative models has emerged as a promising direction for novel drug discovery. However, existing methods require extensive training or fine-tuning using a large dataset, which is often unavailable in real-world generation tasks.

Drug discovery is a complex, multi-objective problem. For a new drug to be considered safe and effective, the molecular identity must interact favorably with the desired target, possess favorable physiochemical properties such as solubility, and be readily synthesizable. Compounding the challenge is the large search space (up to $10^{60}$ molecules). Previous efforts to address these problems utilize high-throughput virtual screening (HTVS) techniques by searching existing molecular databases. Combinatorial approaches have also been proposed to enumerate molecules beyond the space of established drug-like molecule datasets. For example, a genetic-algorithm (GA) based method explores potential new drug candidates via heuristics such as hand-crafted rules and random mutations. Although widely adopted in practice, these methods tend to be inefficient and computationally expensive due to the vast chemical search space. The performance of the combinatorial approaches also heavily depends on the quality of generation rules, which often require task-specific engineering expertise and may limit the diversity of the generated molecules.

To this end, more recent advancements in this technology focus on learning to controllably synthesize molecules with generative models. It usually involves first training an unconditional generative model from millions of existing molecules and then controlling the generative models to synthesize new desired molecules that satisfy one or more property constraints such as high drug-likeliness and high synthesizability. There are three main classes of learning-based molecule generation approaches: (i) reinforcement-learning (RL) based methods; (ii) supervised-learning (SL) based methods; and (iii) latent-optimization (LO) based methods. RL and SL based methods train or fine-tune a pre-trained generative model using the desired properties as reward functions or using molecules with the desired properties as training data. Such methods require heavy task-specific fine-tuning, making them not easily applicable to a wide range of drug discovery tasks. LO based methods, in contrast, learn to find latent representations that correspond to the desired molecules, based on property predictors trained on the generative model's latent space. However, training such latent-space property predictors can be challenging, especially in real-world scenarios where there exist only a limited number of active molecules for training. Moreover, such methods usually necessitate a latent-variable generative model with a compact and structured latent space, making them incompatible with other generative models such as transformer-based architectures. Thus, there is a need to address these issues or other issues in the prior art.

SUMMARY

Embodiments of the present disclosure relate to a machine learning (ML) framework for controllable molecule generation. The ML framework may be referred to as a retrieval-based framework that uses a small set of exemplar molecules, which partially satisfy a desired set of properties, to guide generation of predicted molecules that satisfy the majority or all desired properties. The retrieval mechanism retrieves and fuses the exemplar molecules with an input molecule and implements an iterative refinement process to dynamically update the generated molecules and retrieval database.

In accordance with a first aspect of the present disclosure, a method for generation of candidate molecules using a machine learning framework is provided. The method includes: receiving a representation of an input molecule; and identifying representations of a number of exemplary molecules from a database. The method further includes, for each of the representation of the input molecule and the representations of the number of exemplary molecules from the database, generating, via a trained encoder of the machine learning framework, a corresponding embedding. The method further includes: generating, via a fusion module of the machine learning framework, a fused embedding based on the embedding for the input molecule and the embeddings for the exemplary molecules from the database; and generating, via a trained decoder of the machine learning framework, at least one candidate molecule based on the fused embedding.

In accordance with some embodiments of the first aspect, the fused embedding is generated in accordance with a cross-attention mechanism applied to the embedding for the input molecule and the embeddings for the exemplary molecules from the database.

In accordance with some embodiments of the first aspect, the encoder comprises a bidirectional encoder and the decoder is an autoregressive decoder. In an embodiment, the encoder and decoder are trained using a ZINC dataset.

In accordance with some embodiments of the first aspect, the representations of molecules are encoded in a simplified molecular-input line-entry system (SMILES) string data structure.

In accordance with some embodiments of the first aspect, the method further includes: training the fusion module in accordance with an objective to predict the nearest neighbor of the input molecule in a training data set stored in the database, given as:

$$\mathcal{L}(\theta) = \sum_{i=1}^{\mathcal{B}} CE(DEC(f_{CA}(e_{in}^{(i)}, E_r^{(i)}; \theta)), x_{1NN}^{(i)}).$$

In accordance with some embodiments of the first aspect, the method further includes: calculating, for each molecule stored in the database, a score value in accordance with a score function; and selecting, via a retriever of the machine learning framework, K exemplary molecules from the database as the number of exemplary molecules. The K exemplary molecules are the K molecules in the database having the top score values.

In accordance with some embodiments of the first aspect, each molecule stored in the database has at least one predicted property value of L properties that is greater than a threshold value.

In accordance with some embodiments of the first aspect, the L properties are specified as part of a design criteria for the candidate molecule.

In accordance with some embodiments of the first aspect, the encoder, the decoder, and the fusion module comprise instructions executed by one or more processors of a computer device.

In accordance with some embodiments of the first aspect, the method further includes: generating, based on the fused embedding, a plurality of perturbed embeddings by adding noise to the fused embedding; for each perturbed embedding in the plurality of perturbed embeddings, generating a corresponding candidate molecule using the decoder; calculating a score value for each of the corresponding candidate molecules generated from the perturbed embeddings; and selecting the corresponding candidate molecule with the best score value as a best candidate molecule.

In accordance with some embodiments of the first aspect, the method further includes: calculating a score value for the input molecule; comparing the score for the input molecule with the score value for the best candidate molecule; in response to determining that the score value for the best candidate molecule is greater than the score value for the input molecule, updating the database by adding a representation of the best candidate molecule to the database; and repeating the method for a new input molecule using the updated database.

In accordance with a second aspect of the present disclosure, a system for generating candidate molecules using a machine learning framework is provided. The system includes a memory and at least one processor, communicatively coupled to the memory. The memory stores a database containing representations for a number of molecules. The at least one processor is configured to: receive a representation of an input molecule; identify representations of a number of exemplary molecules from a database; for each of the representation of the input molecule and the representations of the number of exemplary molecules from the database, generate, via a trained encoder of the machine learning framework, a corresponding embedding; generate, via a fusion module of the machine learning framework, a fused embedding based on the embedding for the input molecule and the embeddings for the exemplary molecules from the database; and generate, via a trained decoder of the machine learning framework, at least one candidate molecule based on the fused embedding.

In accordance with some embodiments of the second aspect, the fused embedding is generated in accordance with a cross-attention mechanism applied to the embedding for the input molecule and the embeddings for the exemplary molecules from the database.

In accordance with some embodiments of the second aspect, the encoder comprises a bidirectional encoder and the decoder is an autoregressive decoder.

In accordance with some embodiments of the second aspect, the representations of molecules are encoded in a simplified molecular-input line-entry system (SMILES) string data structure.

In accordance with some embodiments of the second aspect, the at least one processor is further configured to: calculate, for each molecule stored in the database, a score value in accordance with a score function; and select, via a retriever of the machine learning framework, K exemplary molecules from the database as the number of exemplary molecules. The K exemplary molecules are the K molecules in the database having the top score values.

In accordance with some embodiments of the second aspect, the at least one processor is further configured to: generate, based on the fused embedding, a plurality of perturbed embeddings by adding noise to the fused embedding; for each perturbed embedding in the plurality of perturbed embeddings, generate a corresponding candidate molecule using the decoder; calculate a score value for each of the corresponding candidate molecules generated from the perturbed embeddings; and select the corresponding candidate molecule with the best score value as a best candidate molecule.

In accordance with some embodiments of the second aspect, the at least one processor is further configured to: calculate a score value for the input molecule; compare the score for the input molecule with the score value for the best candidate molecule; in response to determining that the score value for the best candidate molecule is greater than the score value for the input molecule, update the database by adding a representation of the best candidate molecule to the database; and repeat the method for a new input molecule using the updated database.

In accordance with a third aspect of the present disclosure, a non-transitory computer readable medium is provided, which stores instructions that, in response to being executed by a computing device, cause the computing device to perform the method of the first aspect.

BRIEF DESCRIPTION OF THE DRAWINGS

The present systems and methods are described in detail below with reference to the attached drawing figures.

DETAILED DESCRIPTION

Systems and methods are disclosed related to a machine learning (ML) framework that is utilized to predict candidate molecules for new drug-discovery. The ML framework includes an encoder-decoder architecture, where the encoder maps a molecule into an embedding representation of the molecule and the decoder generates a new candidate molecule based on a fused embedding, where the fused embedding is generated via a cross-attention mechanism that combines the embedding of the input molecule with embedding representations for a number of exemplary molecules having properties similar to the input molecule. A retrieval database contains molecules that can potentially serve as exemplary molecules to steer the candidate molecule generation task towards a specific design criteria. The construction of the retrieval database is task specific, and usually will contain molecules that at least partially satisfy the design criteria for a given task. The domain knowledge of what molecules meet the design criteria and a technique for selecting molecules that at least partially satisfy the design criteria play an important role in the effectiveness of the ML framework.

The ML framework can play an important role in new drug discovery. By leveraging the molecular structure of known drugs with tested properties, other candidate drugs can be discovered using the ML framework and then tested to find their effectiveness at treating various diseases or symptoms. However, the ML framework can be utilized in other contexts such as predicting new proteins in a medical field context, synthesizing new polymers in a material field context, or so on. In general, the following framework can be applied to different scientific problems in vision tasks, language processing, or others as well as the specific molecule generation task described below. Using the domain expertise of a number of experts in a given field to construct a new retrieval database is the only major design aspect that needs to be created in order to adapt the framework to a new problem, as the training and inference of the models are the same across different tasks.

More illustrative information will now be set forth regarding various optional architectures and features with which the foregoing framework may be implemented, per the desires of the user. It should be strongly noted that the following information is set forth for illustrative purposes and should not be construed as limiting in any manner. Any of the following features may be optionally incorporated with or without the exclusion of other features described.

Figure 1:
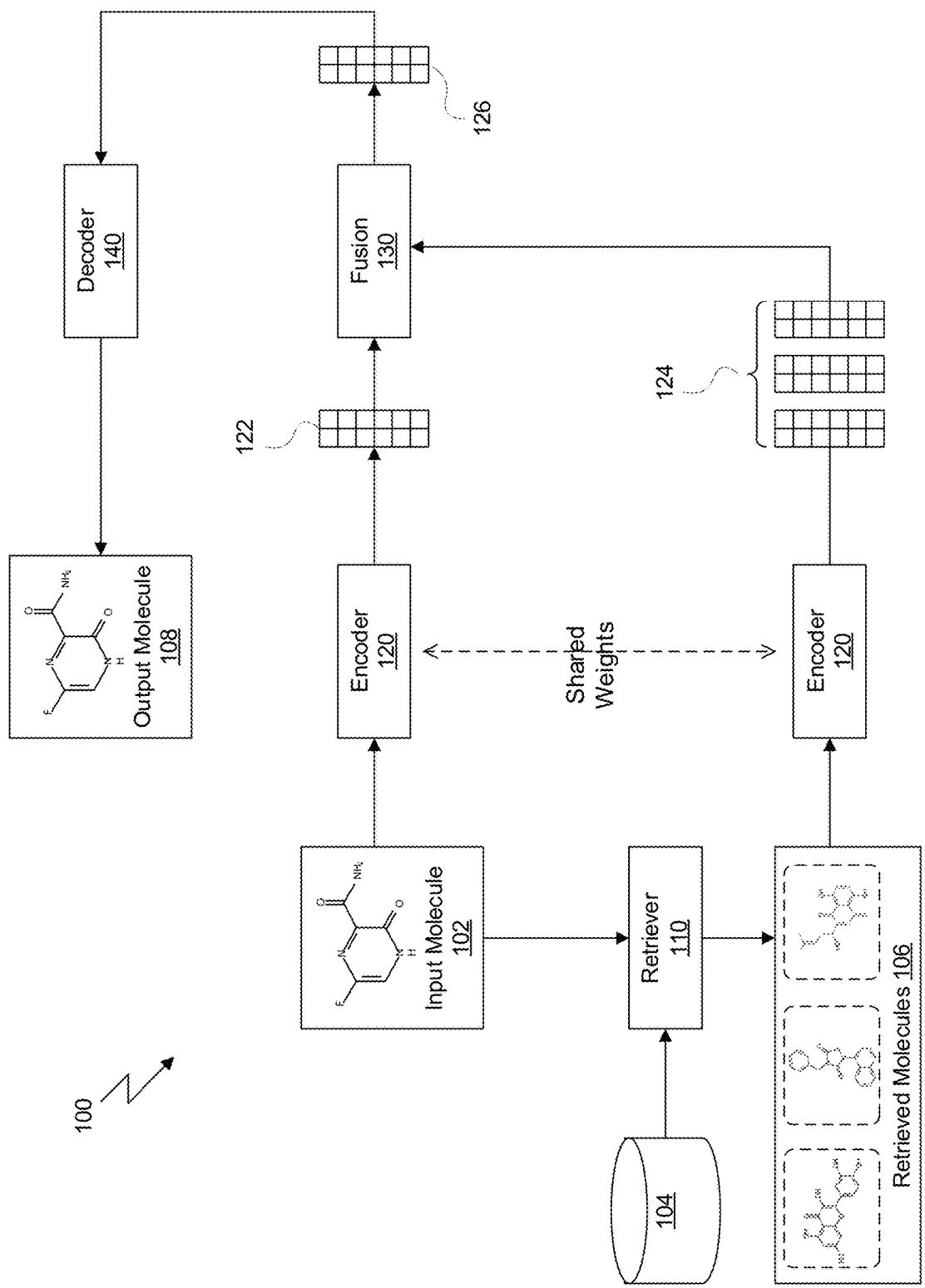
FIG. 1 illustrates a machine learning framework for generating candidate molecules according to some embodiments of the present disclosure.

FIG. 1 illustrates a machine learning (ML) framework 100 for generating candidate molecules according to some embodiments of the present disclosure. The ML framework 100 includes a retriever 110, an encoder 120, a fusion module 130, and a decoder 130. The ML framework 100 is a retrieval-based framework, which uses a small set of exemplary molecules that at least partially satisfy the desired properties of a targeted application, in order to generate new molecules that may, after further evaluation, satisfy a larger percentage of the desired properties. A non-exhaustive list of molecular properties can include potency, metabolic stability, toxicity, and/or effectiveness for a target protein. In this way, it may be possible to use artificial intelligence to help generate new drug candidates or chemicals used in a wide variety of applications. In particular, the ML framework 100 could be used to quickly generate new molecules that treat novel viruses, such as with the recent emergence of the Covid-19 virus (e.g., the SARS-CoV-2 main protease, PDB ID: 7L11) under various design criteria which may include, e.g., properties of similar molecules that were effective at treating other SARS-like viruses.

The retrieval-based mechanism retrieves a sample of exemplary molecules and fuses a latent representation of those molecules with a latent representation of the input molecule. The fused latent representations are then decodes the fused latent representation to generate a new candidate molecule. The fusion module 130 is implemented by a standard cross attention mechanism, and is trained to predict a nearest neighbor of the input molecule. To further improve generation quality and extrapolate beyond the molecules in the molecule database 104, an iterative refinement process can also be implemented that dynamically updates the generated molecules and molecule database 104 during inference.

A molecule database 104 is stored in a computer-readable medium, such as volatile or non-volatile memory. In some embodiments, the molecule database 104 may include a representation of a number of exemplary molecules for a given task. Each molecule may be stored in a data structure that encodes, for example, the atoms, bonds, and structure of the molecule. For example, each atom in the molecule may be stored as a node in a graph data structure. The node may indicate a type of atom (e.g., carbon, oxygen, hydrogen, etc.). Edges between nodes may indicate a bond between two atoms in the molecule, and the edges may encode a type of bond (e.g., covalent, ionic, single/double/triple/quad, polar/nonpolar, etc.). In one embodiment, each molecule may be stored as a graph in a simplified molecular-input line-entry system (SMILES) string data structure, which is a character string in ASCII for representing molecular structure.

In order to generate a new candidate molecule, a user specifies desired design criteria for a molecule generation task, identifies an initial input molecule 102 to be optimized, and constructs the task-specific molecule database 104, which contains a number of exemplary molecules that satisfy at least some of the design criteria. The exemplary molecules may be other molecules that are known to the user to have specific properties. For example, the molecules may be known to be effective at treating other similar viruses to a targeted virus. The ML framework 100 is provided with the input molecule 102. The input molecule 102 can be stored in a similar data structure and format to the molecules stored in the molecule database 104.

The retriever 110 then selects a number of exemplary molecules 106 (e.g., a small sample of exemplary molecules) from the molecule database 104. While the entire set of molecules stored in the molecule database 104 can be used during generation of a candidate molecule, for computational reasons (e.g., memory and efficiency), it is more feasible to select a small portion of the set of stored exemplary molecules to provide guidance to the ML framework 100. In an embodiment, the retriever 110 may select K molecules from the molecule database 104, where K is less than the number of molecules in the molecule database 104. For example, the molecule database 104 may be created with 100 molecules and K may be set to 5 (or any other number suitable for a particular application or computational resources). In some embodiments, the number K may be configurable by a user, and can be dynamically adjusted during inference.

In an embodiment, the retriever 110 can implement a heuristic function to determine which molecules in the molecule database 104. More specifically, a set of molecules is constructed that satisfy a given set of constraints, which can be defined as:

$$\mathcal{X}' = \cap_{\ell=1}^{L} \{x \in \mathcal{X}_R | a_\ell(x) \leq \delta_\ell \} \qquad \text{(Eq 1)}$$

where $\mathcal{X}$ denotes the set of all molecules, $a_\ell(x): \mathcal{X} \to \mathbb{R}$ is a property predictor indexed by $\ell \in [1, \ldots, L]$, and $\delta_\ell \in \mathbb{R}$ is a desired threshold. In other words, the set $\mathcal{X}'$ is a subset of all molecules x in $\mathcal{X}$ that satisfy the constraint where the property predictor for at least one property of L properties is above a corresponding threshold $\delta_\ell$. If the number of molecules in the subset $\mathcal{X}'$ is greater than K, then the retriever 110 is configured to select K molecules with the top property scores (i.e., $\mathcal{X}_R$=top($\mathcal{X}'$, s)), where a score function s(x) is a task-specific weighted average property score given as s(x)=$\sum_{\ell=1}^{L} w_\ell a_\ell(x)$, with weight coefficients $w_\ell$. If the number of molecules in the subset $\mathcal{X}'$ is less than K, then the set of constraints can be relaxed one at a time until the number of molecules in the subset $\mathcal{X}'$ is larger than (or equal to) K. The function of the retriever 110 is to select a set of known molecules, a set of K retrieved exemplary molecules 106, with more desirable properties than the input molecule 102, which will guide the ML framework 110 to generate a new candidate molecule 108 that is similar to the input molecule 102 but which is guided towards the given design criteria (i.e., the given set of constraints in Equation 1 used to create the molecule database 104).

The encoder 120 processes the input molecule 102 to generate an embedding 122 representation of the input molecule 102 in a latent space. An embedding refers to a numerical vector or tensor of a particular dimension. While the representations of the molecules are of varying length depending on the number of atoms or groups of atoms included in the molecule and the types and number of bonds therein, the size of the embedding is fixed for all molecules. The encoder 120 also processes the K exemplary retrieved molecules 106 to generate separate embedding 124 representations for each of the retrieved molecules 106. The encoder 120 and decoder 140 interface between the molecular representation of individual molecules and the embedding representation of those molecules in the latent space. The encoder 120 encodes each molecule into a numerical embedding, and the decoder 140 generates a new candidate molecule from a numerical embedding. The choice of encoder/decoder structure is agnostic, as different pre-trained encoders and decoders can be used in the ML framework 100. In one embodiment, the encoder 120/decoder 140 are a pre-trained denoising autoencoder, such as disclosed in Lewis, M. et al., "BART:Denoising Sequence-to-Sequence Pre-training for Natural Language Generation, Translation, and Comprehension," arXiv:1910.13461 (Oct. 29, 2019), which is herein incorporated by reference in its entirety. As disclosed in Lewis, the encoder 120 is a bidirectional encoder and the decoder 140 is an autoregressive decoder. In an embodiment, the BART model (e.g., MegaMolBART) is pre-trained using an available dataset, such as the ZINC dataset described by Irwin, J. et al., "ZINC—a free database of commercially available compounds for virtual screening," J. of Chem. Information And Modeling, 45(1): 177-182 (December 2004), which is herein incorporated by reference in its entirety. Once trained on this dataset, the encoder 120 and decoder 140 parameters are frozen during inference.

It will be appreciated that the BART model works well with character representations of the molecules, such as provided in the SMILES string data structure disclosed above. However, in other embodiments that use different types of input data structures, other types of encoder/decoder frameworks can be used in lieu of the BART model, which may be trained for those specific input data types.

The fusion module 130 is configured to modify the input molecule towards the targeted design criteria by merging the embedding 122 for the input molecule 102 with embeddings 124 for the exemplary retrieved molecules 106 using a lightweight, standard cross-attention mechanism. The fused embedding 126 is given as:

$$e = f_{CA}(e_{in}, E_r; \theta) = \text{Attn}(\text{Query}(e_{in}), \text{Key}(E_r)) \cdot \text{Value}(E_r), \quad (\text{Eq. 2})$$

where $f_{CA}$ represents the cross attention function with parameters $\theta$, and $e_{in}$ and $E_r$ are the embedding 122 and embeddings 126, respectively. The functions Attn( ), Query( ), Key( ), and Value( ) compute the cross attention weights and the query, key, and value matrices, respectively.

Given a pre-trained encoder 120 and decoder 140, the ML framework 100 can be trained for molecule generation by keeping the parameters of the encoder 120 and decoder 140 frozen, while updating the cross attention weights of the fusion module 130. Furthermore, a conventional likelihood objective that reconstructs the input molecule is not appropriate for training the ML framework 100 as a perfect input reconstruction does not rely on the retrieved exemplary molecules 106 at all. Consequently, the objective of the ML framework 100 is to predict the nearest neighbor of the input molecule based on the set of exemplary molecules from the entire molecular space, as given by the following loss function:

$$\mathcal{L}(\theta) = \sum_{i=1}^{\mathcal{B}} CE(DEC(f_{CA}(e_{in}^{(i)}, E_r^{(i)}; \theta)), x_{1NN}^{(i)}), \quad (\text{Eq. 3})$$

where CE is the cross entropy loss function, $x_{1NN}$ represents the nearest neighbor of the input $x_{in}$, $\mathcal{B}$ is the batch size, and i indexes the input molecule. During training, the full training data set is used as the molecule database 104, and an input molecule 102 is selected at random from the training data set. The nearest neighbor to the selected input molecule 102 in the training data set is then used as the ground truth output, $x_{1NN}$, and the next K−1 nearest neighbors of the input molecule 102 are selected as the set of retrieved exemplary molecules 106. The input molecule 102 and K−1 nearest neighbors are processed by the pre-trained encoder 120, fused via the fusion module 130 to generate the fused embedding 126, which is then processed by the decoder 140 to generate a new candidate molecule 108. The cross entropy loss is calculated by comparing the candidate molecule 108 to the ground truth output $x_{1NN}$. The process is repeated for $\mathcal{B}$ different input molecules 102, and then the parameters of the fusion module 130 are updated based on the combined cross entropy losses, as shown in Equation 3. The training described above is not task specific (as the full training data set is used for molecule database 104 rather than only a subset of molecules that match a target design criteria), yet the training forces the fusion module 130 to use similarity to the input molecule as a proxy criterion.

Once the ML framework 100 has been trained, inference can be performed by adjusting the molecule database 104 to only include those molecules that are known to meet a target design criteria. An input molecule 102 can be selected, and the ML framework 100 generates a new candidate molecule 108 as the output, which represents a similar molecule to the input molecule 102, but guided by similarity to the group of K molecules selected from the molecule database 104.

An iterative approach to inference can be used where, during each iteration the molecule database 104 is updated with the new candidate molecule 108. Updating the molecule database 104 allows for unconstrained optimization scenarios where the best property values of molecules in the molecule database 104 are not fixed to those properties that are known at the start of inference. In an embodiment, an iterative refinement process can be performed by, during each iteration, generating the fused embedding 126 based on the input molecule 102 and the retrieved exemplary molecules 106. The fused embedding 126 is then randomly perturbed M times, and each of the M perturbed embeddings is then decoded by the decoder 140 to generate M candidate molecules 108. A score is calculated for each of the M candidate molecules 108, to select the molecule in the M candidate molecules as the best candidate molecule, and the input molecule 102 is replaced in the next iteration with the best candidate molecule if the score for the best candidate molecule is better than a score for the input molecule. If none of the M generated candidate molecules has a score better than a score for the input molecule, then the input molecule and the molecule database 104 stays the same for the next iteration, where new random perturbations of the fused embedding 126 will result in M new candidate molecules. The iterative process can also be stopped if either a maximum number of iterations is reached, or if the generated best candidate molecule 108 satisfies some design criteria.

Figure 2A:
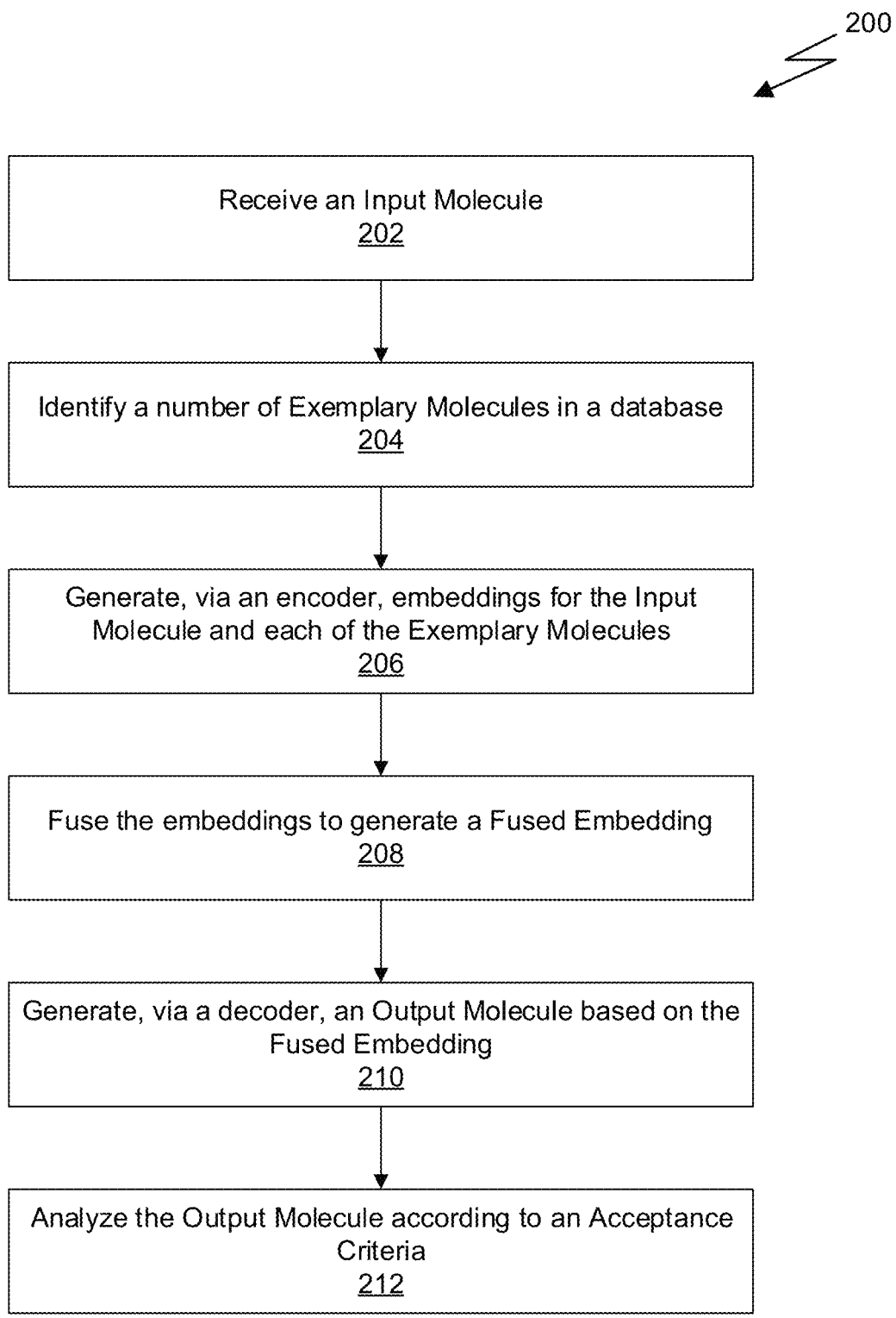
FIG. 2A is a flow chart of a method for performing a molecule generation task, in accordance with some embodiments of the present disclosure.

FIG. 2A is a flow chart of a method 200 for performing a molecule generation task, in accordance with some embodiments of the present disclosure. The method 200 may be performed using the ML framework 100 described above. Furthermore, elements of the ML framework 100 may be implemented using one or more computing devices. The elements may be implemented using hardware, firmware, software, or any combination of hardware or software. In some embodiments, the method 200 can be implemented by one or more processors configured to execute instructions that implement one or more elements of the ML framework 100.

At 202, a representation of an input molecule is received. In an embodiment, the representation can be in the form of a data structure. For example, the representation of a molecule can be encoded in a simplified molecular-input line-entry system (SMILES) string data structure. In other embodiments, the representation of a molecule can be encoded in a graph data structure that includes nodes and edges, where each node represents an atom or group of atoms of the molecule and each edge represents a bond between one or more nodes.

At 204, representations for a number of exemplary molecules in a database are identified. In an embodiment, a retriever 110 of the ML framework 100 selects representations of molecules from the database that have the top score values, where a score value is calculated for each molecule in the database in accordance with a score function. In an embodiment, the molecules having the K highest score values are selected as the number of exemplary molecules.

At 206, embeddings are generated for the input molecule and each of the exemplary molecules. In an embodiment, a pre-trained encoder 120 (e.g., a bidirectional encoder such as the encoder from the BART model) is used to process the representation for a molecule to generate an embedding for that molecule in a latent space. The embedding can be a numerical vector or tensor of a pre-defined dimension. Each embedding can be generated sequentially using a single instance of the encoder, or multiple embeddings can be generated in parallel using different instances of the encoder that share the same weights or parameters.

At 208, the embeddings are fused to generate a fused embedding. In an embodiment, a fusion module 130 is trained to fuse the embedding for the input molecule with the embeddings for the K exemplary molecules using a cross-attention mechanism. The fusion module may be trained in accordance with an objective to predict the nearest neighbor of the input molecule in a training data set stored in the database 104.

At 210, an output molecule (i.e., a candidate molecule) is generated based on the fused embedding. In an embodiment, a pre-trained decoder 140 (e.g., an autoregressive decoder such as the decoder from the BART model) is used to process the fused embedding to generate a representation of the output molecule.

At 212, the output molecule is analyzed according to an acceptance criteria. In some embodiments, a score value is calculated for the output molecule in accordance with a score function. The score value for the output molecule may be compared to the score value for the input molecule. If the score value for the output molecule is greater than the score value for the input molecule, then the acceptance criteria is met and the output molecule is accepted as a newly generated candidate molecule for further evaluation. However, if the score value for the output molecule is less than the score value for the input molecule, then the output molecule may be discarded and a new candidate molecule may be generated for, e.g., a new input molecule. In another embodiment, the score value for the output molecule may be compared against a threshold value. If the score value is greater than the threshold value, then the acceptance criteria is met. Otherwise, if the score value is less than the threshold value, then the output molecule may be discarded.

In some embodiments, the score value can be related to a measure of synthesizability. In other words, the heuristic function for the score value can be related to an estimate of the difficulty to synthesize the output molecule using known molecule synthesizing techniques. If the output molecule is likely difficult or impossible to synthesize, then the score value may be low and the output molecule can be discarded.

Figure 2B:
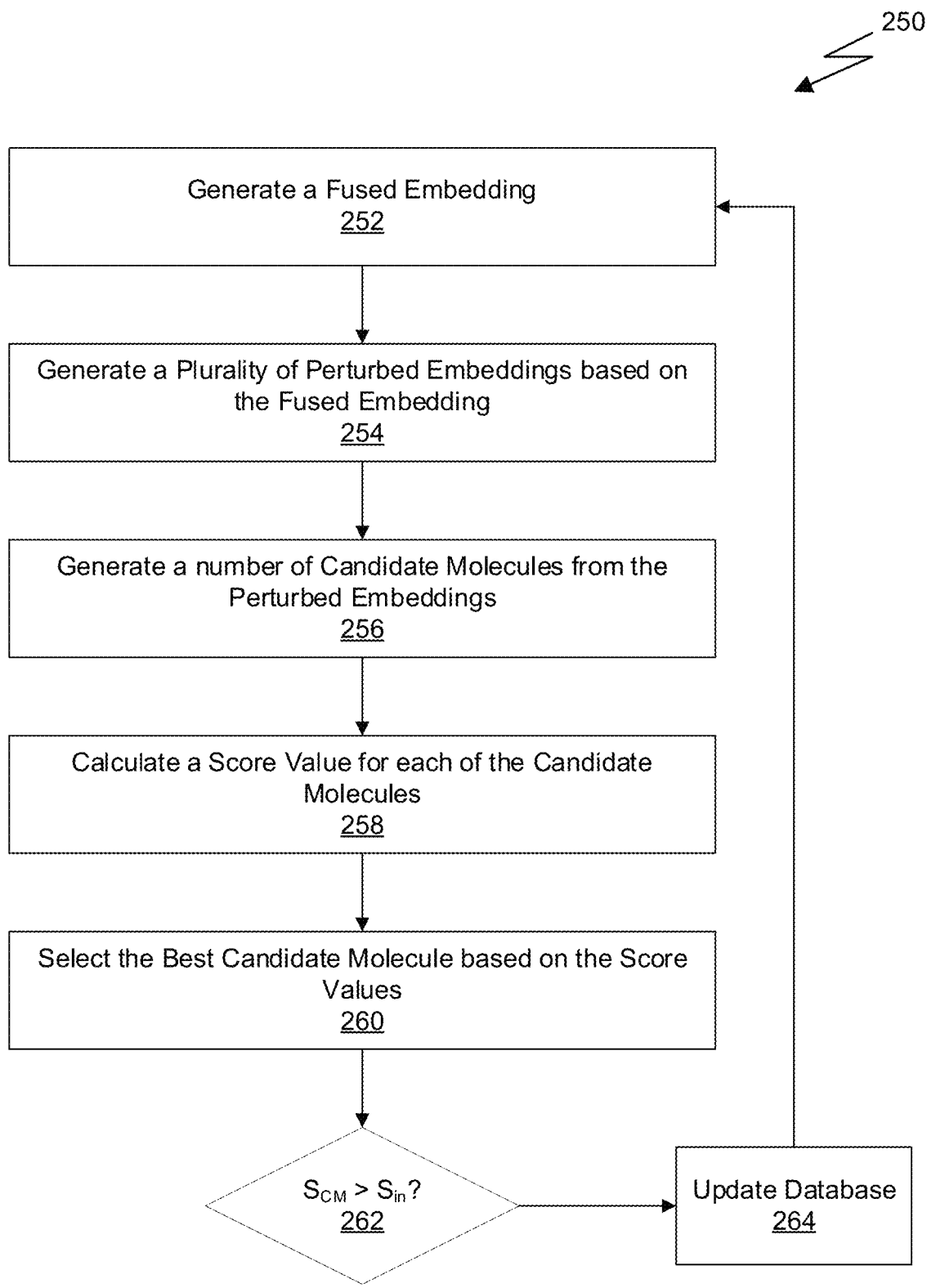
FIG. 2B is a flow chart of a method for performing a molecule generation task using an iterative optimization technique, in accordance with some embodiments of the present disclosure.

FIG. 2B is a flow chart of a method 250 for performing a molecule generation task using an iterative optimization technique, in accordance with some embodiments of the present disclosure. The method 250 may be performed using the ML framework 100 described above. Furthermore, elements of the ML framework 100 may be implemented using one or more computing devices. The elements may be implemented using hardware, firmware, software, or any combination of hardware or software. In some embodiments, the method 250 can be implemented by one or more processors configured to execute instructions that implement one or more elements of the ML framework 100.

The method 250 can be employed in an iterative optimization process during inference. During each iteration, a number of candidate molecules are generated for a particular input molecule. The candidate molecules are evaluated and a best candidate molecule is selected and compared against the input molecule. If the best candidate molecule meets the acceptance criteria, then the database of exemplary molecules can be dynamically updated and another iteration is performed.

At 252, a fused embedding is generated similar to steps 202 to 208 of method 200, described in detail above.

At 254, a plurality of perturbed embeddings are generated based on the fused embedding. For example, the number of perturbed embeddings generated for the fused embedding can be 50. In an embodiment, each of the perturbed embeddings is generated by adding a small amount of noise to the fused embedding to generate an embedding that is slightly offset in distance in the latent space from the fused embedding. For example, the fused embedding can be perturbed by independent random isotropic Gaussian noise with a standard deviation of 1. A size of the noise can be preset (i.e., fixed) or can be dynamically adjusted based on a distribution of the embeddings for the K exemplary molecules. In other words, the choice of standard deviation can be set in accordance with a function related to the distributions of embeddings for the molecules in the database 104.

At 256, a number of candidate molecules are generated using the decoder. The decoder 140 may be used to process each perturbed embedding to generate a different candidate molecule. The new candidate molecules can be generated sequentially or in parallel using different instances of the decoder. Each instance of the decoder shares the same weights or parameters.

At 258, a score value is calculated for each of the corresponding candidate molecules generated from the perturbed embeddings. The score value may be calculated in accordance with a score function, similar to as described in step 212 in method 200, above.

At 260, the candidate molecule associated with the best score value is selected as the best candidate molecule.

At 262, the score value for the best candidate molecule is compared against the score value for the input molecule, which may have been calculated during a previous iteration. Else, the score value for the input molecule can also be calculated in accordance with the score function. If the score value for the best candidate molecule is greater than the score value for the input molecule, then, at 264, the database 104 is dynamically updated by adding a representation of the best candidate molecule to the database 104. Otherwise, the best candidate molecule is discarded.

After 264, the method 250 returns to step 252, where a new iteration is performed using the updated database and/or a new input molecule. In some embodiments, the new input molecule is the best candidate molecule from a previous iteration which passed the acceptance criteria (i.e., score value for best candidate molecule greater than score value for input molecule). Otherwise, the input molecule from the previous iteration can be reused during the next iteration.

It will be appreciated that the method 250 can be run for a fixed number of iterations (e.g., 100), each iteration generating a number of perturbed candidate molecules based on a generated fused embedding, and then updating the database with the best candidate molecule as long as said molecule meets some acceptance criteria. Method 250 may also be stopped early (e.g., at an earlier iteration before the max number of iterations) when some other criteria is met, such as where a score value for the best candidate molecule meets or exceeds some pre-defined threshold.

Figure 3:
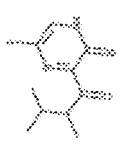
FIG. 3 illustrates results from various inferencing tasks using the trained ML framework, in accordance with some embodiments

FIG. 3 illustrates results from various inferencing tasks using the trained ML framework, in accordance with some embodiments. A 2D graph visualization of the input molecule, optimized output molecule, and a similarity score comparing the input molecule to the output molecule is shown. The input molecules used here include Favipiravir, Bromhexine, PX-12, and Disulfiram. These input molecules are used by way of example only and should not be construed as limiting the scope of the claimed embodiments.

An example system suitable for use in implementing some embodiments of the present disclosure is set forth below. It should be understood that this and other arrangements described herein are set forth only as examples. Other arrangements and elements (e.g., machines, interfaces, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory. Furthermore, persons of ordinary skill in the art will understand that any system that performs the operations of the method 100 is within the scope and spirit of embodiments of the present disclosure.

Parallel Processing Architecture

Figure 4:
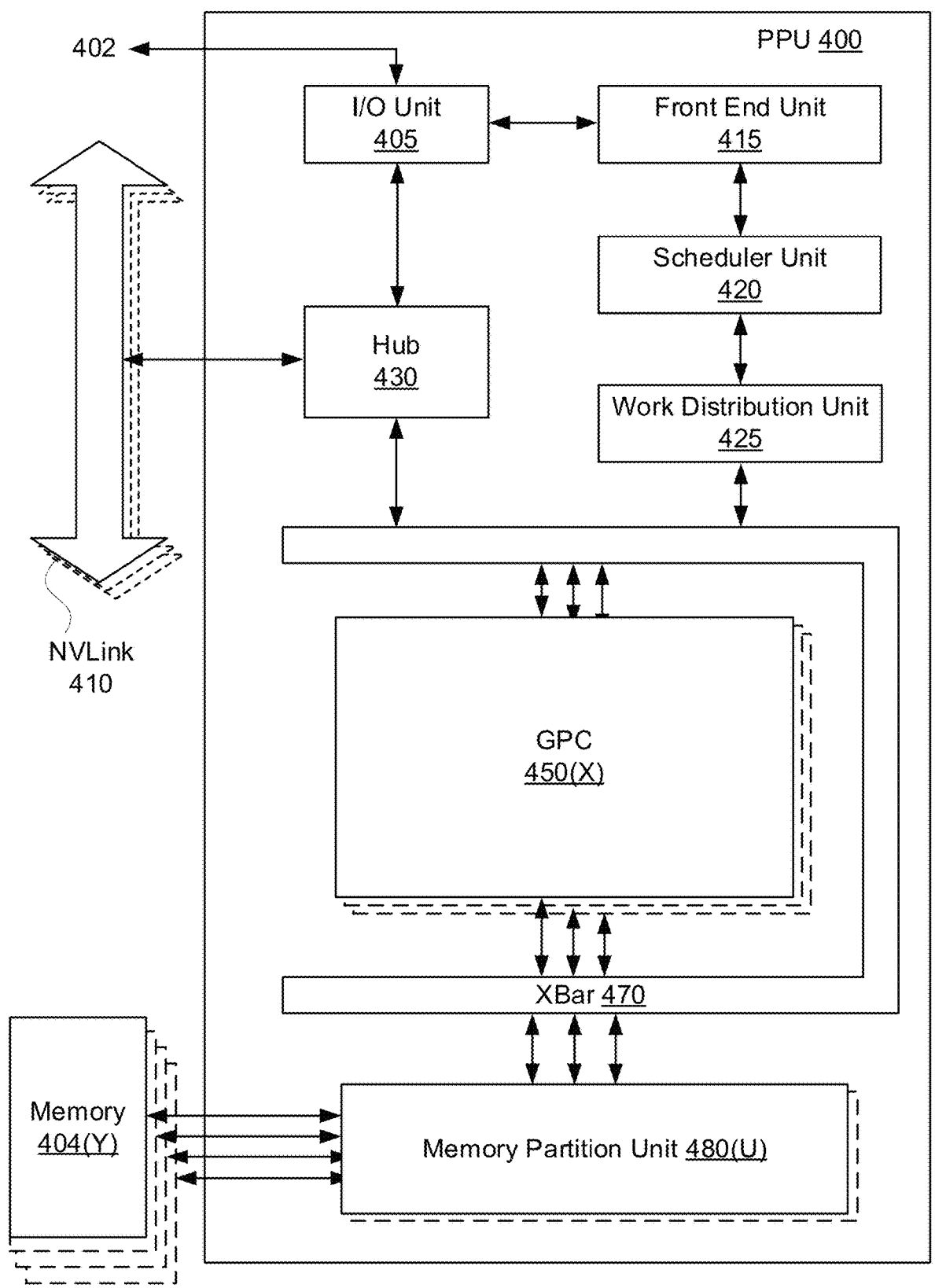
FIG. 4 illustrates an example parallel processing unit suitable for use in implementing some embodiments of the present disclosure.

FIG. 4 illustrates a parallel processing unit (PPU) 400, in accordance with an embodiment. In an embodiment, the PPU 400 is a multi-threaded processor that is implemented on one or more integrated circuit devices. The PPU 400 is a latency hiding architecture designed to process many threads in parallel. A thread (e.g., a thread of execution) is an instantiation of a set of instructions configured to be executed by the PPU 400. In an embodiment, the PPU 400 is a graphics processing unit (GPU) configured to implement a graphics rendering pipeline for processing three-dimensional (3D) graphics data in order to generate two-dimensional (2D) image data for display on a display device. In other embodiments, the PPU 400 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

One or more PPUs 400 may be configured to accelerate thousands of High Performance Computing (HPC), data center, cloud computing, and machine learning applications. The PPU 400 may be configured to accelerate numerous deep learning systems and applications for autonomous vehicles, simulation, computational graphics such as ray or path tracing, deep learning, high-accuracy speech, image, and text recognition systems, intelligent video analytics, molecular simulations, drug discovery, disease diagnosis, weather forecasting, big data analytics, astronomy, molecular dynamics simulation, financial modeling, robotics, factory automation, real-time language translation, online search optimizations, and personalized user recommendations, and the like.

As shown in FIG. 4, the PPU 400 includes an Input/Output (I/O) unit 405, a front end unit 415, a scheduler unit 420, a work distribution unit 425, a hub 430, a crossbar (Xbar) 470, one or more general processing clusters (GPCs) 450, and one or more memory partition units 480. The PPU 400 may be connected to a host processor or other PPUs 400 via one or more high-speed NVLink 410 interconnect. The PPU 400 may be connected to a host processor or other peripheral devices via an interconnect 402. The PPU 400 may also be connected to a local memory 404 comprising a number of memory devices. In an embodiment, the local memory may comprise a number of dynamic random access memory (DRAM) devices. The DRAM devices may be configured as a high-bandwidth memory (HBM) subsystem, with multiple DRAM dies stacked within each device.

The NVLink 410 interconnect enables systems to scale and include one or more PPUs 400 combined with one or more CPUs, supports cache coherence between the PPUs 400 and CPUs, and CPU mastering. Data and/or commands may be transmitted by the NVLink 410 through the hub 430 to/from other units of the PPU 400 such as one or more copy engines, a video encoder, a video decoder, a power management unit, etc. (not explicitly shown). The NVLink 410 is described in more detail in conjunction with FIG. 5B.

The I/O unit 405 is configured to transmit and receive communications (e.g., commands, data, etc.) from a host processor (not shown) over the interconnect 402. The I/O unit 405 may communicate with the host processor directly via the interconnect 402 or through one or more intermediate devices such as a memory bridge. In an embodiment, the I/O unit 405 may communicate with one or more other processors, such as one or more the PPUs 400 via the interconnect 402. In an embodiment, the I/O unit 405 implements a Peripheral Component Interconnect Express (PCIe) interface for communications over a PCIe bus and the interconnect 402 is a PCIe bus. In alternative embodiments, the I/O unit 405 may implement other types of well-known interfaces for communicating with external devices.

The I/O unit 405 decodes packets received via the interconnect 402. In an embodiment, the packets represent commands configured to cause the PPU 400 to perform various operations. The I/O unit 405 transmits the decoded commands to various other units of the PPU 400 as the commands may specify. For example, some commands may be transmitted to the front end unit 415. Other commands may be transmitted to the hub 430 or other units of the PPU 400 such as one or more copy engines, a video encoder, a video decoder, a power management unit, etc. (not explicitly shown). In other words, the I/O unit 405 is configured to route communications between and among the various logical units of the PPU 400.

In an embodiment, a program executed by the host processor encodes a command stream in a buffer that provides workloads to the PPU 400 for processing. A workload may comprise several instructions and data to be processed by those instructions. The buffer is a region in a memory that is accessible (e.g., read/write) by both the host processor and the PPU 400. For example, the I/O unit 405 may be configured to access the buffer in a system memory connected to the interconnect 402 via memory requests transmitted over the interconnect 402. In an embodiment, the host processor writes the command stream to the buffer and then transmits a pointer to the start of the command stream to the PPU 400. The front end unit 415 receives pointers to one or more command streams. The front end unit 415 manages the one or more streams, reading commands from the streams and forwarding commands to the various units of the PPU 400.

The front end unit 415 is coupled to a scheduler unit 420 that configures the various GPCs 450 to process tasks defined by the one or more streams. The scheduler unit 420 is configured to track state information related to the various tasks managed by the scheduler unit 420. The state may indicate which GPC 450 a task is assigned to, whether the task is active or inactive, a priority level associated with the task, and so forth. The scheduler unit 420 manages the execution of a plurality of tasks on the one or more GPCs 450.

The scheduler unit 420 is coupled to a work distribution unit 425 that is configured to dispatch tasks for execution on the GPCs 450. The work distribution unit 425 may track a number of scheduled tasks received from the scheduler unit 420. In an embodiment, the work distribution unit 425 manages a pending task pool and an active task pool for each of the GPCs 450. As a GPC 450 finishes the execution of a task, that task is evicted from the active task pool for the GPC 450 and one of the other tasks from the pending task pool is selected and scheduled for execution on the GPC 450. If an active task has been idle on the GPC 450, such as while waiting for a data dependency to be resolved, then the active task may be evicted from the GPC 450 and returned to the pending task pool while another task in the pending task pool is selected and scheduled for execution on the GPC 450.

In an embodiment, a host processor executes a driver kernel that implements an application programming interface (API) that enables one or more applications executing on the host processor to schedule operations for execution on the PPU 400. In an embodiment, multiple compute applications are simultaneously executed by the PPU 400 and the PPU 400 provides isolation, quality of service (QoS), and independent address spaces for the multiple compute applications. An application may generate instructions (e.g., API calls) that cause the driver kernel to generate one or more tasks for execution by the PPU 400. The driver kernel outputs tasks to one or more streams being processed by the PPU 400. Each task may comprise one or more groups of related threads, referred to herein as a warp. In an embodiment, a warp comprises 32 related threads that may be executed in parallel. Cooperating threads may refer to a plurality of threads including instructions to perform the task and that may exchange data through shared memory. The tasks may be allocated to one or more processing units within a GPC 450 and instructions are scheduled for execution by at least one warp.

The work distribution unit 425 communicates with the one or more GPCs 450 via XBar 470. The XBar 470 is an interconnect network that couples many of the units of the PPU 400 to other units of the PPU 400. For example, the XBar 470 may be configured to couple the work distribution unit 425 to a particular GPC 450. Although not shown explicitly, one or more other units of the PPU 400 may also be connected to the XBar 470 via the hub 430.

The tasks are managed by the scheduler unit 420 and dispatched to a GPC 450 by the work distribution unit 425. The GPC 450 is configured to process the task and generate results. The results may be consumed by other tasks within the GPC 450, routed to a different GPC 450 via the XBar 470, or stored in the memory 404. The results can be written to the memory 404 via the memory partition units 480, which implement a memory interface for reading and writing data to/from the memory 404. The results can be transmitted to another PPU 400 or CPU via the NVLink 410. In an embodiment, the PPU 400 includes a number U of memory partition units 480 that is equal to the number of separate and distinct memory devices of the memory 404 coupled to the PPU 400. Each GPC 450 may include a memory management unit to provide translation of virtual addresses into physical addresses, memory protection, and arbitration of memory requests. In an embodiment, the memory management unit provides one or more translation lookaside buffers (TLBs) for performing translation of virtual addresses into physical addresses in the memory 404.

In an embodiment, the memory partition unit 480 includes a Raster Operations (ROP) unit, a level two (L2) cache, and a memory interface that is coupled to the memory 404. The memory interface may implement 32, 64, 128, 1024-bit data buses, or the like, for high-speed data transfer. The PPU 400 may be connected to up to Y memory devices, such as high bandwidth memory stacks or graphics double-data-rate, version 5, synchronous dynamic random access memory, or other types of persistent storage. In an embodiment, the memory interface implements an HBM2 memory interface and Y equals half U. In an embodiment, the HBM2 memory stacks are located on the same physical package as the PPU 400, providing substantial power and area savings compared with conventional GDDR5 SDRAM systems. In an embodiment, each HBM2 stack includes four memory dies and Y equals 4, with each HBM2 stack including two 128-bit channels per die for a total of 8 channels and a data bus width of 1024 bits.

In an embodiment, the memory 404 supports Single-Error Correcting Double-Error Detecting (SECDED) Error Correction Code (ECC) to protect data. ECC provides higher reliability for compute applications that are sensitive to data corruption. Reliability is especially important in large-scale cluster computing environments where PPUs 400 process very large datasets and/or run applications for extended periods.

In an embodiment, the PPU 400 implements a multi-level memory hierarchy. In an embodiment, the memory partition unit 480 supports a unified memory to provide a single unified virtual address space for CPU and PPU 400 memory, enabling data sharing between virtual memory systems. In an embodiment the frequency of accesses by a PPU 400 to memory located on other processors is traced to ensure that memory pages are moved to the physical memory of the PPU 400 that is accessing the pages more frequently. In an embodiment, the NVLink 410 supports address translation services allowing the PPU 400 to directly access a CPU's page tables and providing full access to CPU memory by the PPU 400.

In an embodiment, copy engines transfer data between multiple PPUs 400 or between PPUs 400 and CPUs. The copy engines can generate page faults for addresses that are not mapped into the page tables. The memory partition unit 480 can then service the page faults, mapping the addresses into the page table, after which the copy engine can perform the transfer. In a conventional system, memory is pinned (e.g., non-pageable) for multiple copy engine operations between multiple processors, substantially reducing the available memory. With hardware page faulting, addresses can be passed to the copy engines without worrying if the memory pages are resident, and the copy process is transparent.

Data from the memory 404 or other system memory may be fetched by the memory partition unit 480 and stored in the L2 cache 460, which is located on-chip and is shared between the various GPCs 450. As shown, each memory partition unit 480 includes a portion of the L2 cache associated with a corresponding memory 404. Lower level caches may then be implemented in various units within the GPCs 450. For example, each of the processing units within a GPC 450 may implement a level one (L1) cache. The L1 cache is private memory that is dedicated to a particular processing unit. The L2 cache 460 is coupled to the memory interface 470 and the XBar 470 and data from the L2 cache may be fetched and stored in each of the L1 caches for processing.

In an embodiment, the processing units within each GPC 450 implement a SIMD (Single-Instruction, Multiple-Data) architecture where each thread in a group of threads (e.g., a warp) is configured to process a different set of data based on the same set of instructions. All threads in the group of threads execute the same instructions. In another embodiment, the processing unit implements a SIMT (Single-Instruction, Multiple Thread) architecture where each thread in a group of threads is configured to process a different set of data based on the same set of instructions, but where individual threads in the group of threads are allowed to diverge during execution. In an embodiment, a program counter, call stack, and execution state is maintained for each warp, enabling concurrency between warps and serial execution within warps when threads within the warp diverge. In another embodiment, a program counter, call stack, and execution state is maintained for each individual thread, enabling equal concurrency between all threads, within and between warps. When execution state is main-tained for each individual thread, threads executing the same instructions may be converged and executed in parallel for maximum efficiency.

Cooperative Groups is a programming model for organizing groups of communicating threads that allows developers to express the granularity at which threads are communicating, enabling the expression of richer, more efficient parallel decompositions. Cooperative launch APIs support synchronization amongst thread blocks for the execution of parallel algorithms. Conventional programming models provide a single, simple construct for synchronizing cooperating threads: a barrier across all threads of a thread block (e.g., the syncthreads( ) function). However, programmers would often like to define groups of threads at smaller than thread block granularities and synchronize within the defined groups to enable greater performance, design flexibility, and software reuse in the form of collective group-wide function interfaces.

Cooperative Groups enables programmers to define groups of threads explicitly at sub-block (e.g., as small as a single thread) and multi-block granularities, and to perform collective operations such as synchronization on the threads in a cooperative group. The programming model supports clean composition across software boundaries, so that libraries and utility functions can synchronize safely within their local context without having to make assumptions about convergence. Cooperative Groups primitives enable new patterns of cooperative parallelism, including producer-consumer parallelism, opportunistic parallelism, and global synchronization across an entire grid of thread blocks.

Each processing unit includes a large number (e.g., 128, etc.) of distinct processing cores (e.g., functional units) that may be fully-pipelined, single-precision, double-precision, and/or mixed precision and include a floating point arithmetic logic unit and an integer arithmetic logic unit. In an embodiment, the floating point arithmetic logic units implement the IEEE 754-2008 standard for floating point arithmetic. In an embodiment, the cores include 64 single-precision (32-bit) floating point cores, 64 integer cores, 32 double-precision (64-bit) floating point cores, and 8 tensor cores.

Tensor cores configured to perform matrix operations. In particular, the tensor cores are configured to perform deep learning matrix arithmetic, such as GEMM (matrix-matrix multiplication) for convolution operations during neural network training and inferencing. In an embodiment, each tensor core operates on a 4×4 matrix and performs a matrix multiply and accumulate operation $D=A\times B+C$, where A, B, C, and D are 4×4 matrices.

In an embodiment, the matrix multiply inputs A and B may be integer, fixed-point, or floating point matrices, while the accumulation matrices C and D may be integer, fixed-point, or floating point matrices of equal or higher bitwidths. In an embodiment, tensor cores operate on one, four, or eight bit integer input data with 32-bit integer accumulation. The 8-bit integer matrix multiply requires 1024 operations and results in a full precision product that is then accumulated using 32-bit integer addition with the other intermediate products for a 8×8×16 matrix multiply. In an embodiment, tensor Cores operate on 16-bit floating point input data with 32-bit floating point accumulation. The 16-bit floating point multiply requires 64 operations and results in a full precision product that is then accumulated using 32-bit floating point addition with the other intermediate products for a 4×4×4 matrix multiply. In practice, Tensor Cores are used to perform much larger two-dimensional or higher dimensional matrix operations, built up from these smaller elements. An API, such as CUDA 9 C++ API, exposes specialized matrix load, matrix multiply and accumulate, and matrix store operations to efficiently use Tensor Cores from a CUDA-C++ program. At the CUDA level, the warp-level interface assumes 16×16 size matrices spanning all 32 threads of the warp.

Each processing unit may also comprise M special function units (SFUs) that perform special functions (e.g., attribute evaluation, reciprocal square root, and the like). In an embodiment, the SFUs may include a tree traversal unit configured to traverse a hierarchical tree data structure. In an embodiment, the SFUs may include texture unit configured to perform texture map filtering operations. In an embodiment, the texture units are configured to load texture maps (e.g., a 2D array of texels) from the memory 404 and sample the texture maps to produce sampled texture values for use in shader programs executed by the processing unit. In an embodiment, the texture maps are stored in shared memory that may comprise or include an L1 cache. The texture units implement texture operations such as filtering operations using mip-maps (e.g., texture maps of varying levels of detail). In an embodiment, each processing unit includes two texture units.

Each processing unit also comprises N load store units (LSUs) that implement load and store operations between the shared memory and the register file. Each processing unit includes an interconnect network that connects each of the cores to the register file and the LSU to the register file, shared memory. In an embodiment, the interconnect network is a crossbar that can be configured to connect any of the cores to any of the registers in the register file and connect the LSUs to the register file and memory locations in shared memory.

The shared memory is an array of on-chip memory that allows for data storage and communication between the processing units and between threads within a processing unit. In an embodiment, the shared memory comprises 128 KB of storage capacity and is in the path from each of the processing units to the memory partition unit 480. The shared memory can be used to cache reads and writes. One or more of the shared memory, L1 cache, L2 cache, and memory 404 are backing stores.

Combining data cache and shared memory functionality into a single memory block provides the best overall performance for both types of memory accesses. The capacity is usable as a cache by programs that do not use shared memory. For example, if shared memory is configured to use half of the capacity, texture and load/store operations can use the remaining capacity. Integration within the shared memory enables the shared memory to function as a high-throughput conduit for streaming data while simultaneously providing high-bandwidth and low-latency access to frequently reused data.

When configured for general purpose parallel computation, a simpler configuration can be used compared with graphics processing. Specifically, fixed function graphics processing units, are bypassed, creating a much simpler programming model. In the general purpose parallel computation configuration, the work distribution unit 425 assigns and distributes blocks of threads directly to the processing units within the GPCs 450. Threads execute the same program, using a unique thread ID in the calculation to ensure each thread generates unique results, using the processing unit(s) to execute the program and perform calculations, shared memory to communicate between threads, and the LSU to read and write global memory through the shared memory and the memory partition unit 480. When configured for general purpose parallel computation, the processing units can also write commands that the scheduler unit 420 can use to launch new work on the processing units.

The PPUs 400 may each include, and/or be configured to perform functions of, one or more processing cores and/or components thereof, such as Tensor Cores (TCs), Tensor Processing Units (TPUs), Pixel Visual Cores (PVCs), Ray Tracing (RT) Cores, Vision Processing Units (VPUs), Graphics Processing Clusters (GPCs), Texture Processing Clusters (TPCs), Streaming Multiprocessors (SMs), Tree Traversal Units (TTUs), Artificial Intelligence Accelerators (AIAs), Deep Learning Accelerators (DLAs), Arithmetic-Logic Units (ALUs), Application-Specific Integrated Circuits (ASICs), Floating Point Units (FPUs), input/output (I/O) elements, peripheral component interconnect (PCI) or peripheral component interconnect express (PCIe) elements, and/or the like.

The PPU 400 may be included in a desktop computer, a laptop computer, a tablet computer, servers, supercomputers, a smart-phone (e.g., a wireless, hand-held device), personal digital assistant (PDA), a digital camera, a vehicle, a head mounted display, a hand-held electronic device, and the like. In an embodiment, the PPU 400 is embodied on a single semiconductor substrate. In another embodiment, the PPU 400 is included in a system-on-a-chip (SoC) along with one or more other devices such as additional PPUs 400, the memory 404, a reduced instruction set computer (RISC) CPU, a memory management unit (MMU), a digital-to-analog converter (DAC), and the like.

In an embodiment, the PPU 400 may be included on a graphics card that includes one or more memory devices. The graphics card may be configured to interface with a PCIe slot on a motherboard of a desktop computer. In yet another embodiment, the PPU 400 may be an integrated graphics processing unit (iGPU) or parallel processor included in the chipset of the motherboard. In yet another embodiment, the PPU 400 may be realized in reconfigurable hardware. In yet another embodiment, parts of the PPU 400 may be realized in reconfigurable hardware.

Exemplary Computing System

Systems with multiple GPUs and CPUs are used in a variety of industries as developers expose and leverage more parallelism in applications such as artificial intelligence computing. High-performance GPU-accelerated systems with tens to many thousands of compute nodes are deployed in data centers, research facilities, and supercomputers to solve ever larger problems. As the number of processing devices within the high-performance systems increases, the communication and data transfer mechanisms need to scale to support the increased bandwidth.

Figure 5A:
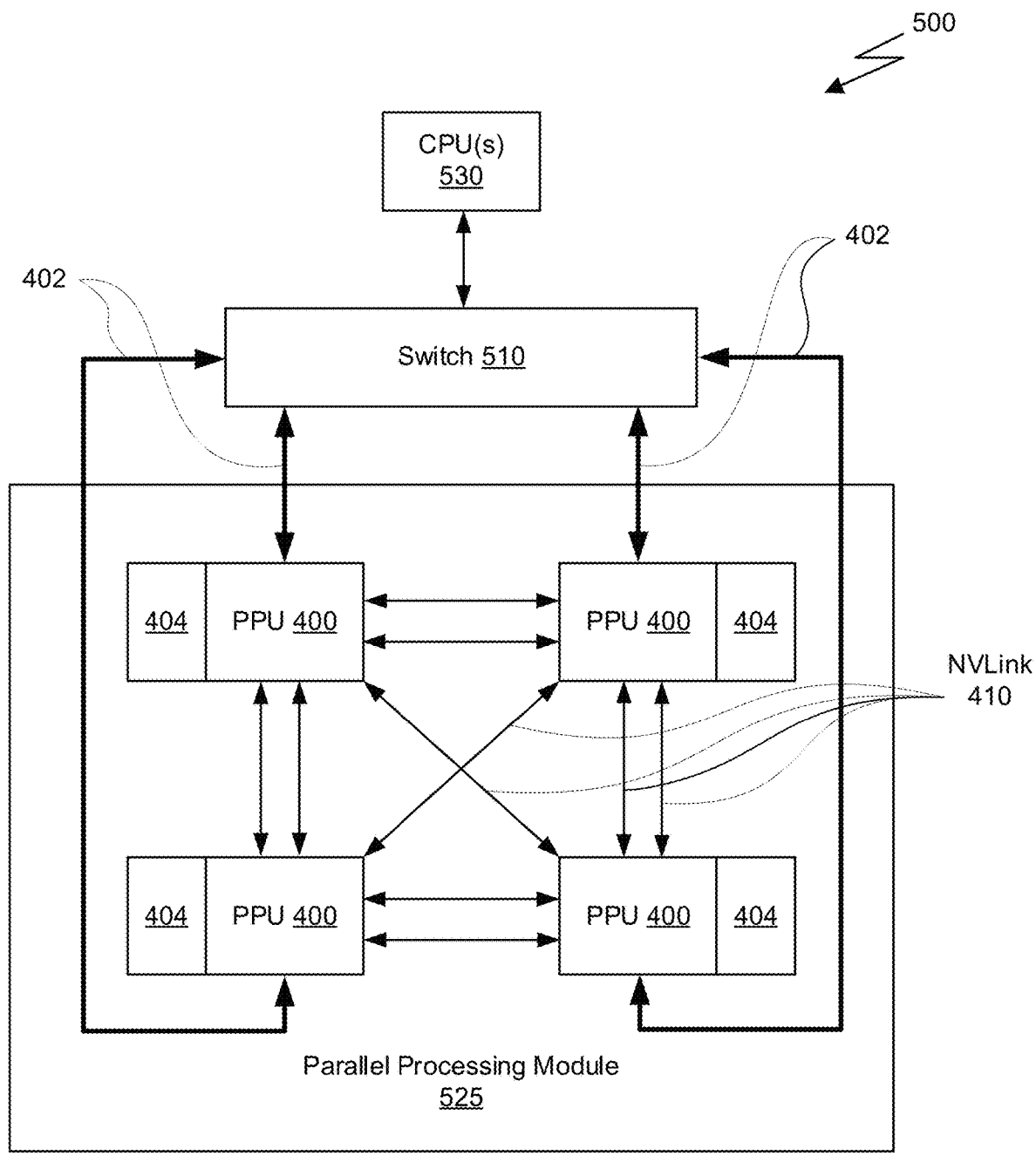
FIG. 5A is a conceptual diagram of a processing system implemented using the PPU of FIG. 4, suitable for use in implementing some embodiments of the present disclosure.

FIG. 5A is a conceptual diagram of a processing system 500 implemented using the PPU 400 of FIG. 4, in accordance with an embodiment. The exemplary system 565 may be configured to implement the method 100 shown in FIG. 1. The processing system 500 includes a CPU 530, switch 510, and multiple PPUs 400, and respective memories 404.

Figure 5B:
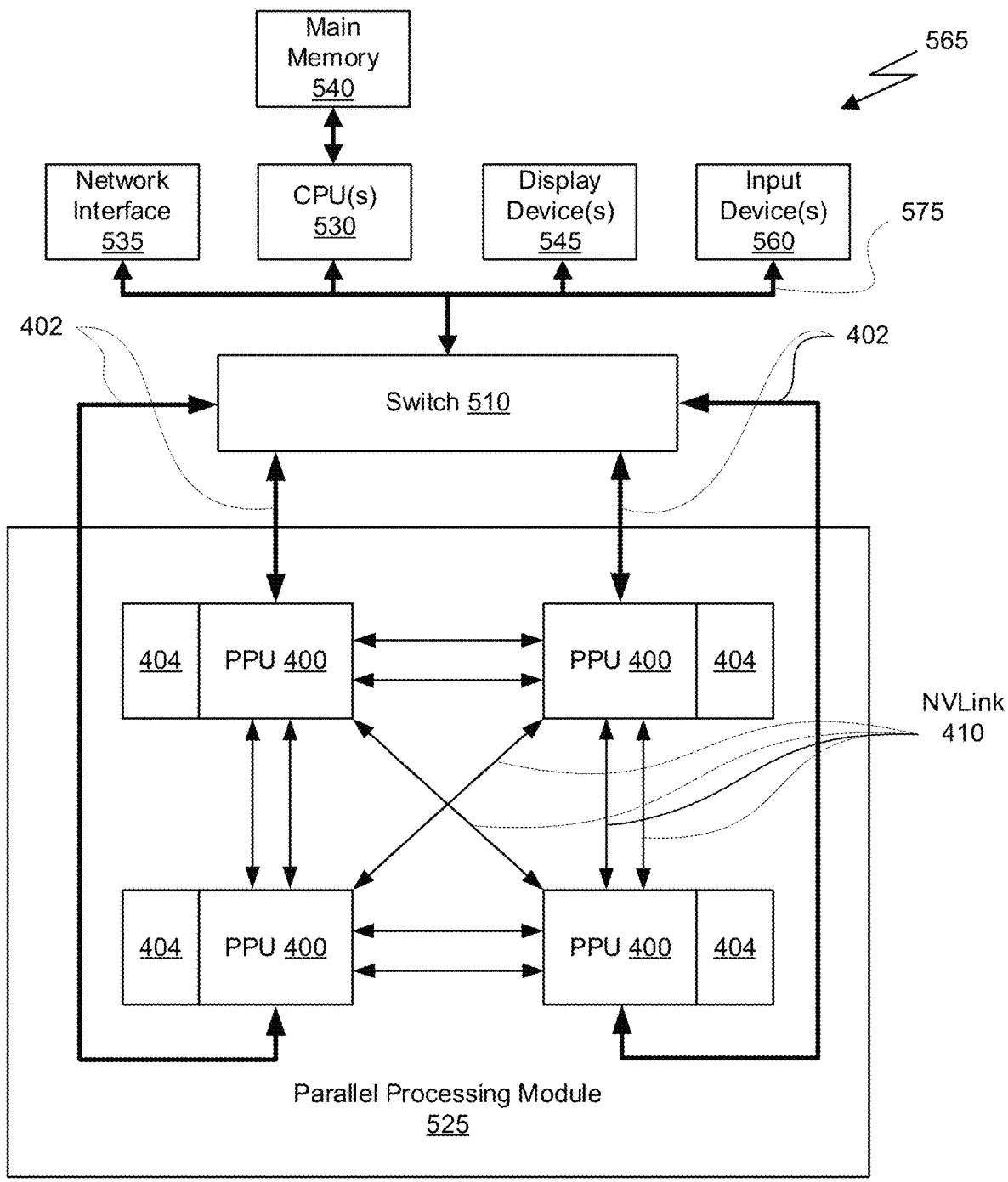
FIG. 5B illustrates an exemplary system in which the various architecture and/or functionality of the various previous embodiments may be implemented.

The NVLink 410 provides high-speed communication links between each of the PPUs 400. Although a particular number of NVLink 410 and interconnect 402 connections are illustrated in FIG. 5B, the number of connections to each PPU 400 and the CPU 530 may vary. The switch 510 interfaces between the interconnect 402 and the CPU 530. The PPUs 400, memories 404, and NVLinks 410 may be situated on a single semiconductor platform to form a parallel processing module 525. In an embodiment, the switch 510 supports two or more protocols to interface between various different connections and/or links.

In another embodiment (not shown), the NVLink 410 provides one or more high-speed communication links between each of the PPUs 400 and the CPU 530 and the switch 510 interfaces between the interconnect 402 and each of the PPUs 400. The PPUs 400, memories 404, and interconnect 402 may be situated on a single semiconductor platform to form a parallel processing module 525. In yet another embodiment (not shown), the interconnect 402 provides one or more communication links between each of the PPUs 400 and the CPU 530 and the switch 510 interfaces between each of the PPUs 400 using the NVLink 410 to provide one or more high-speed communication links between the PPUs 400. In another embodiment (not shown), the NVLink 410 provides one or more high-speed communication links between the PPUs 400 and the CPU 530 through the switch 510. In yet another embodiment (not shown), the interconnect 402 provides one or more communication links between each of the PPUs 400 directly. One or more of the NVLink 410 high-speed communication links may be implemented as a physical NVLink interconnect or either an on-chip or on-die interconnect using the same protocol as the NVLink 410.

In the context of the present description, a single semiconductor platform may refer to a sole unitary semiconductor-based integrated circuit fabricated on a die or chip. It should be noted that the term single semiconductor platform may also refer to multi-chip modules with increased connectivity which simulate on-chip operation and make substantial improvements over utilizing a conventional bus implementation. Of course, the various circuits or devices may also be situated separately or in various combinations of semiconductor platforms per the desires of the user. Alternately, the parallel processing module 525 may be implemented as a circuit board substrate and each of the PPUs 400 and/or memories 404 may be packaged devices. In an embodiment, the CPU 530, switch 510, and the parallel processing module 525 are situated on a single semiconductor platform.

In an embodiment, the signaling rate of each NVLink 410 is 20 to 25 Gigabits/second and each PPU 400 includes six NVLink 410 interfaces (as shown in FIG. 5A, five NVLink 410 interfaces are included for each PPU 400). Each NVLink 410 provides a data transfer rate of 25 Gigabytes/second in each direction, with six links providing 400 Gigabytes/second. The NVLinks 410 can be used exclusively for PPU-to-PPU communication as shown in FIG. 5A, or some combination of PPU-to-PPU and PPU-to-CPU, when the CPU 530 also includes one or more NVLink 410 interfaces.

In an embodiment, the NVLink 410 allows direct load/store/atomic access from the CPU 530 to each PPU's 400 memory 404. In an embodiment, the NVLink 410 supports coherency operations, allowing data read from the memories 404 to be stored in the cache hierarchy of the CPU 530, reducing cache access latency for the CPU 530. In an embodiment, the NVLink 410 includes support for Address Translation Services (ATS), allowing the PPU 400 to directly access page tables within the CPU 530. One or more of the NVLinks 410 may also be configured to operate in a low-power mode.

FIG. 5B illustrates an exemplary system 565 in which the various architecture and/or functionality of the various previous embodiments may be implemented. The exemplary system 565 may be configured to implement the method 100 shown in FIG. 1.

As shown, a system 565 is provided including at least one central processing unit 530 that is connected to a communication bus 575. The communication bus 575 may directly or indirectly couple one or more of the following devices: main memory 540, network interface 535, CPU(s) 530, display device(s) 545, input device(s) 560, switch 510, and parallel processing system 525. The communication bus 575 may be implemented using any suitable protocol and may represent one or more links or busses, such as an address bus, a data bus, a control bus, or a combination thereof. The communication bus 575 may include one or more bus or link types, such as an industry standard architecture (ISA) bus, an extended industry standard architecture (EISA) bus, a video electronics standards association (VESA) bus, a peripheral component interconnect (PCI) bus, a peripheral component interconnect express (PCIe) bus, HyperTransport, and/or another type of bus or link. In some embodiments, there are direct connections between components. As an example, the CPU(s) 530 may be directly connected to the main memory 540. Further, the CPU(s) 530 may be directly connected to the parallel processing system 525. Where there is direct, or point-to-point connection between components, the communication bus 575 may include a PCIe link to carry out the connection. In these examples, a PCI bus need not be included in the system 565.

Figure 5C:
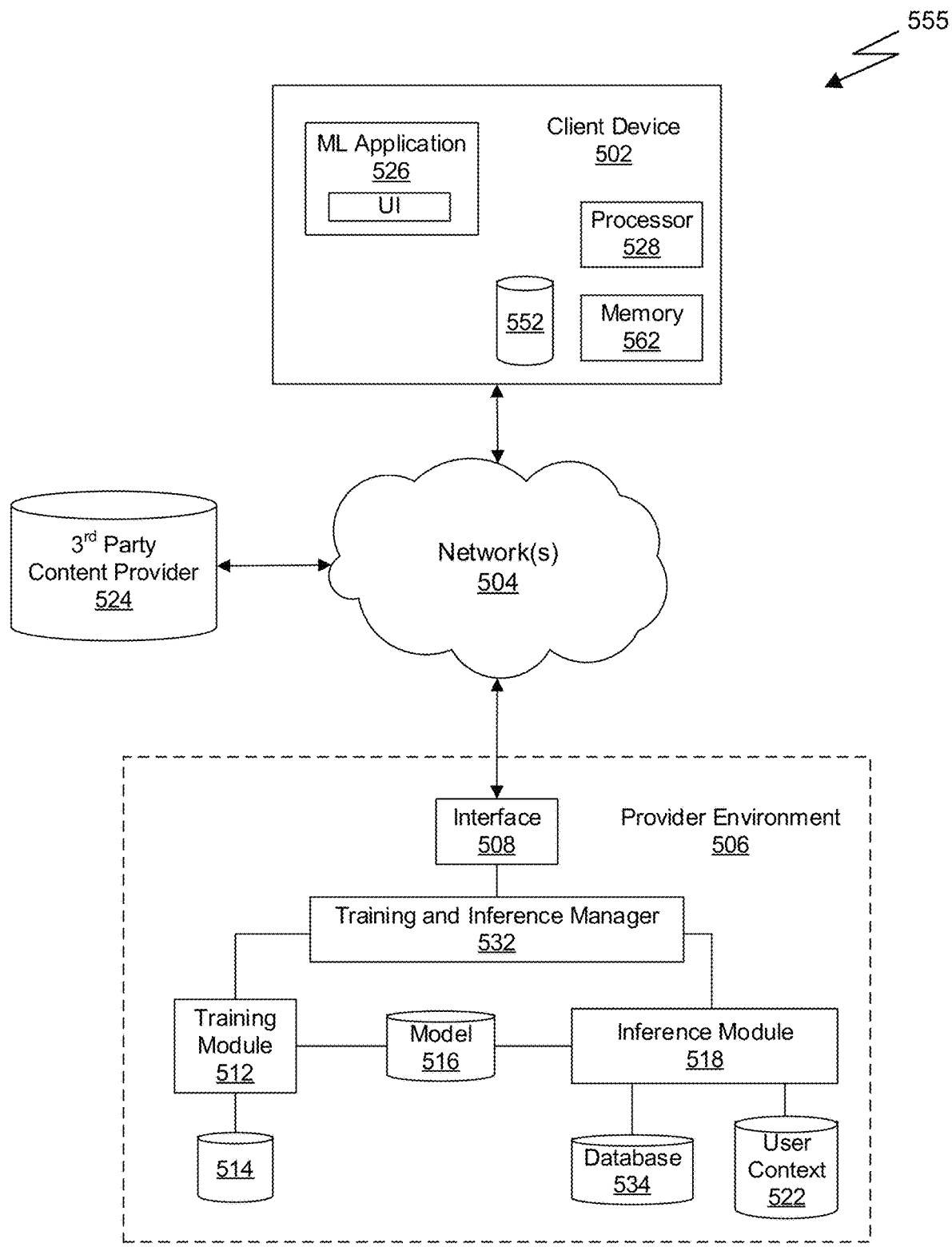
FIG. 5C illustrates components of an exemplary system that can be used to train and utilize machine learning, in at least one embodiment.

Although the various blocks of FIG. 5C are shown as connected via the communication bus 575 with lines, this is not intended to be limiting and is for clarity only. For example, in some embodiments, a presentation component, such as display device(s) 545, may be considered an I/O component, such as input device(s) 560 (e.g., if the display is a touch screen). As another example, the CPU(s) 530 and/or parallel processing system 525 may include memory (e.g., the main memory 540 may be representative of a storage device in addition to the parallel processing system 525, the CPUs 530, and/or other components). In other words, the computing device of FIG. 5C is merely illustrative. Distinction is not made between such categories as "workstation," "server," "laptop," "desktop," "tablet," "client device," "mobile device," "hand-held device," "game console," "electronic control unit (ECU)," "virtual reality system," and/or other device or system types, as all are contemplated within the scope of the computing device of FIG. 5C.

The system 565 also includes a main memory 540. Control logic (software) and data are stored in the main memory 540 which may take the form of a variety of computer-readable media. The computer-readable media may be any available media that may be accessed by the system 565. The computer-readable media may include both volatile and nonvolatile media, and removable and non-removable media. By way of example, and not limitation, the computer-readable media may comprise computer-storage media and communication media.

The computer-storage media may include both volatile and nonvolatile media and/or removable and non-removable media implemented in any method or technology for storage of information such as computer-readable instructions, data structures, program modules, and/or other data types. For example, the main memory 540 may store computer-readable instructions (e.g., that represent a program(s) and/or a program element(s), such as an operating system. Computer-storage media may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by system 565. As used herein, computer storage media does not comprise signals per se.

The computer storage media may embody computer-readable instructions, data structures, program modules, and/or other data types in a modulated data signal such as a carrier wave or other transport mechanism and includes any information delivery media. The term "modulated data signal" may refer to a signal that has one or more of its characteristics set or changed in such a manner as to encode information in the signal. By way of example, and not limitation, the computer storage media may include wired media such as a wired network or direct-wired connection, and wireless media such as acoustic, RF, infrared and other wireless media. Combinations of any of the above should also be included within the scope of computer-readable media.

Computer programs, when executed, enable the system 565 to perform various functions. The CPU(s) 530 may be configured to execute at least some of the computer-readable instructions to control one or more components of the system 565 to perform one or more of the methods and/or processes described herein. The CPU(s) 530 may each include one or more cores (e.g., one, two, four, eight, twenty-eight, seventy-two, etc.) that are capable of handling a multitude of software threads simultaneously. The CPU(s) 530 may include any type of processor, and may include different types of processors depending on the type of system 565 implemented (e.g., processors with fewer cores for mobile devices and processors with more cores for servers). For example, depending on the type of system 565, the processor may be an Advanced RISC Machines (ARM) processor implemented using Reduced Instruction Set Computing (RISC) or an x86 processor implemented using Complex Instruction Set Computing (CISC). The system 565 may include one or more CPUs 530 in addition to one or more microprocessors or supplementary co-processors, such as math co-processors.

In addition to or alternatively from the CPU(s) 530, the parallel processing module 525 may be configured to execute at least some of the computer-readable instructions to control one or more components of the system 565 to perform one or more of the methods and/or processes described herein. The parallel processing module 525 may be used by the system 565 to render graphics (e.g., 3D graphics) or perform general purpose computations. For example, the parallel processing module 525 may be used for General-Purpose computing on GPUs (GPGPU). In embodiments, the CPU(s) 530 and/or the parallel processing module 525 may discretely or jointly perform any combination of the methods, processes and/or portions thereof.

The system 565 also includes input device(s) 560, the parallel processing system 525, and display device(s) 545. The display device(s) 545 may include a display (e.g., a monitor, a touch screen, a television screen, a heads-up-display (HUD), other display types, or a combination thereof), speakers, and/or other presentation components. The display device(s) 545 may receive data from other components (e.g., the parallel processing system 525, the CPU(s) 530, etc.), and output the data (e.g., as an image, video, sound, etc.).

The network interface 535 may enable the system 565 to be logically coupled to other devices including the input devices 560, the display device(s) 545, and/or other components, some of which may be built in to (e.g., integrated in) the system 565. Illustrative input devices 560 include a microphone, mouse, keyboard, joystick, game pad, game controller, satellite dish, scanner, printer, wireless device, etc. The input devices 560 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the system 565. The system 565 may be include depth cameras, such as stereoscopic camera systems, infrared camera systems, RGB camera systems, touchscreen technology, and combinations of these, for gesture detection and recognition. Additionally, the system 565 may include accelerometers or gyroscopes (e.g., as part of an inertia measurement unit (IMU)) that enable detection of motion. In some examples, the output of the accelerometers or gyroscopes may be used by the system 565 to render immersive augmented reality or virtual reality.

Further, the system 565 may be coupled to a network (e.g., a telecommunications network, local area network (LAN), wireless network, wide area network (WAN) such as the Internet, peer-to-peer network, cable network, or the like) through a network interface 535 for communication purposes. The system 565 may be included within a distributed network and/or cloud computing environment.

The network interface 535 may include one or more receivers, transmitters, and/or transceivers that enable the system 565 to communicate with other computing devices via an electronic communication network, included wired and/or wireless communications. The network interface 535 may include components and functionality to enable communication over any of a number of different networks, such as wireless networks (e.g., Wi-Fi, Z-Wave, Bluetooth, Bluetooth LE, ZigBee, etc.), wired networks (e.g., communicating over Ethernet or InfiniBand), low-power wide-area networks (e.g., LoRaWAN, SigFox, etc.), and/or the Internet.

The system 565 may also include a secondary storage (not shown). The secondary storage 610 includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner. The system 565 may also include a hard-wired power supply, a battery power supply, or a combination thereof (not shown). The power supply may provide power to the system 565 to enable the components of the system 565 to operate.

Each of the foregoing modules and/or devices may even be situated on a single semiconductor platform to form the system 565. Alternately, the various modules may also be situated separately or in various combinations of semiconductor platforms per the desires of the user. While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

Example Network Environments

Network environments suitable for use in implementing embodiments of the disclosure may include one or more client devices, servers, network attached storage (NAS), other backend devices, and/or other device types. The client devices, servers, and/or other device types (e.g., each device) may be implemented on one or more instances of the processing system 500 of FIG. 5A and/or exemplary system 565 of FIG. 5B—e.g., each device may include similar components, features, and/or functionality of the processing system 500 and/or exemplary system 565.

Components of a network environment may communicate with each other via a network(s), which may be wired, wireless, or both. The network may include multiple networks, or a network of networks. By way of example, the network may include one or more Wide Area Networks (WANs), one or more Local Area Networks (LANs), one or more public networks such as the Internet and/or a public switched telephone network (PSTN), and/or one or more private networks. Where the network includes a wireless telecommunications network, components such as a base station, a communications tower, or even access points (as well as other components) may provide wireless connectivity.

Compatible network environments may include one or more peer-to-peer network environments—in which case a server may not be included in a network environment—and one or more client-server network environments—in which case one or more servers may be included in a network environment. In peer-to-peer network environments, functionality described herein with respect to a server(s) may be implemented on any number of client devices.

In at least one embodiment, a network environment may include one or more cloud-based network environments, a distributed computing environment, a combination thereof, etc. A cloud-based network environment may include a framework layer, a job scheduler, a resource manager, and a distributed file system implemented on one or more of servers, which may include one or more core network servers and/or edge servers. A framework layer may include a framework to support software of a software layer and/or one or more application(s) of an application layer. The software or application(s) may respectively include web-based service software or applications. In embodiments, one or more of the client devices may use the web-based service software or applications (e.g., by accessing the service software and/or applications via one or more application programming interfaces (APIs)). The framework layer may be, but is not limited to, a type of free and open-source software web application framework such that may use a distributed file system for large-scale data processing (e.g., "big data").

A cloud-based network environment may provide cloud computing and/or cloud storage that carries out any combination of computing and/or data storage functions described herein (or one or more portions thereof). Any of these various functions may be distributed over multiple locations from central or core servers (e.g., of one or more data centers that may be distributed across a state, a region, a country, the globe, etc.). If a connection to a user (e.g., a client device) is relatively close to an edge server(s), a core server(s) may designate at least a portion of the functionality to the edge server(s). A cloud-based network environment may be private (e.g., limited to a single organization), may be public (e.g., available to many organizations), and/or a combination thereof (e.g., a hybrid cloud environment).

The client device(s) may include at least some of the components, features, and functionality of the example processing system 500 of FIG. 5B and/or exemplary system 565 of FIG. 5C. By way of example and not limitation, a client device may be embodied as a Personal Computer (PC), a laptop computer, a mobile device, a smartphone, a tablet computer, a smart watch, a wearable computer, a Personal Digital Assistant (PDA), an MP3 player, a virtual reality headset, a Global Positioning System (GPS) or device, a video player, a video camera, a surveillance device or system, a vehicle, a boat, a flying vessel, a virtual machine, a drone, a robot, a handheld communications device, a hospital device, a gaming device or system, an entertainment system, a vehicle computer system, an embedded system controller, a remote control, an appliance, a consumer electronic device, a workstation, an edge device, any combination of these delineated devices, or any other suitable device.

Machine Learning

Deep neural networks (DNNs) developed on processors, such as the PPU 400 have been used for diverse use cases, from self-driving cars to faster drug development, from automatic image captioning in online image databases to smart real-time language translation in video chat applications. Deep learning is a technique that models the neural learning process of the human brain, continually learning, continually getting smarter, and delivering more accurate results more quickly over time. A child is initially taught by an adult to correctly identify and classify various shapes, eventually being able to identify shapes without any coaching. Similarly, a deep learning or neural learning system needs to be trained in object recognition and classification for it get smarter and more efficient at identifying basic objects, occluded objects, etc., while also assigning context to objects.

At the simplest level, neurons in the human brain look at various inputs that are received, importance levels are assigned to each of these inputs, and output is passed on to other neurons to act upon. An artificial neuron is the most basic model of a neural network.

A deep neural network (DNN) model includes multiple layers of many connected nodes (e.g., Boltzmann machines, radial basis functions, convolutional layers, etc.) that can be trained with enormous amounts of input data to quickly solve complex problems with high accuracy. In one example, a first layer of the DNN model breaks down an input image of an automobile into various sections and looks for basic patterns such as lines and angles. The second layer assembles the lines to look for higher level patterns such as wheels, windshields, and mirrors. The next layer identifies the type of vehicle, and the final few layers generate a label for the input image, identifying the model of a specific automobile brand.

Once the DNN is trained, the DNN can be deployed and used to identify and classify objects or patterns in a process known as inference. Examples of inference (the process through which a DNN extracts useful information from a given input) include identifying handwritten numbers on checks deposited into ATM machines, identifying images of friends in photos, delivering movie recommendations to over fifty million users, identifying and classifying different types of automobiles, pedestrians, and road hazards in driverless cars, or translating human speech in real-time.

During training, data flows through the DNN in a forward propagation phase until a prediction is produced that indicates a label corresponding to the input. If the neural network does not correctly label the input, then errors between the correct label and the predicted label are analyzed, and the weights are adjusted for each feature during a backward propagation phase until the DNN correctly labels the input and other inputs in a training dataset. Training complex neural networks requires massive amounts of parallel computing performance, including floating-point multiplications and additions that are supported by the PPU 400. Inferencing is less compute-intensive than training, being a latency-sensitive process where a trained neural network is applied to new inputs it has not seen before to classify images, detect emotions, identify recommendations, recognize and translate speech, and generally infer new information.

Neural networks rely heavily on matrix math operations, and complex multi-layered networks require tremendous amounts of floating-point performance and bandwidth for both efficiency and speed. With thousands of processing cores, optimized for matrix math operations, and delivering tens to hundreds of TFLOPS of performance, the PPU 400 is a computing platform capable of delivering performance required for deep neural network-based artificial intelligence and machine learning applications.

Furthermore, images generated applying one or more of the techniques disclosed herein may be used to train, test, or certify DNNs used to recognize objects and environments in the real world. Such images may include scenes of roadways, factories, buildings, urban settings, rural settings, humans, animals, and any other physical object or real-world setting. Such images may be used to train, test, or certify DNNs that are employed in machines or robots to manipulate, handle, or modify physical objects in the real world. Furthermore, such images may be used to train, test, or certify DNNs that are employed in autonomous vehicles to navigate and move the vehicles through the real world. Additionally, images generated applying one or more of the techniques disclosed herein may be used to convey information to users of such machines, robots, and vehicles.

FIG. 5C illustrates components of an exemplary system 555 that can be used to train and utilize machine learning, in accordance with at least one embodiment. As will be discussed, various components can be provided by various combinations of computing devices and resources, or a single computing system, which may be under control of a single entity or multiple entities. Further, aspects may be triggered, initiated, or requested by different entities. In at least one embodiment training of a neural network might be instructed by a provider associated with provider environment 506, while in at least one embodiment training might be requested by a customer or other user having access to a provider environment through a client device 502 or other such resource. In at least one embodiment, training data (or data to be analyzed by a trained neural network) can be provided by a provider, a user, or a third party content provider 524. In at least one embodiment, client device 502 may be a vehicle or object that is to be navigated on behalf of a user, for example, which can submit requests and/or receive instructions that assist in navigation of a device.

In at least one embodiment, requests are able to be submitted across at least one network 504 to be received by a provider environment 506. In at least one embodiment, a client device may be any appropriate electronic and/or computing devices enabling a user to generate and send such requests, such as, but not limited to, desktop computers, notebook computers, computer servers, smartphones, tablet computers, gaming consoles (portable or otherwise), computer processors, computing logic, and set-top boxes. Network(s) 504 can include any appropriate network for transmitting a request or other such data, as may include Internet, an intranet, an Ethernet, a cellular network, a local area network (LAN), a wide area network (WAN), a personal area network (PAN), an ad hoc network of direct wireless connections among peers, and so on.

In at least one embodiment, requests can be received at an interface layer 508, which can forward data to a training and inference manager 532, in this example. The training and inference manager 532 can be a system or service including hardware and software for managing requests and service corresponding data or content, in at least one embodiment, the training and inference manager 532 can receive a request to train a neural network, and can provide data for a request to a training module 512. In at least one embodiment, training module 512 can select an appropriate model or neural network to be used, if not specified by the request, and can train a model using relevant training data. In at least one embodiment, training data can be a batch of data stored in a training data repository 514, received from client device 502, or obtained from a third party provider 524. In at least one embodiment, training module 512 can be responsible for training data. A neural network can be any appropriate network, such as a recurrent neural network (RNN) or convolutional neural network (CNN). Once a neural network is trained and successfully evaluated, a trained neural network can be stored in a model repository 516, for example, that may store different models or networks for users, applications, or services, etc. In at least one embodiment, there may be multiple models for a single application or entity, as may be utilized based on a number of different factors.

In at least one embodiment, at a subsequent point in time, a request may be received from client device 502 (or another such device) for content (e.g., path determinations) or data that is at least partially determined or impacted by a trained neural network. This request can include, for example, input data to be processed using a neural network to obtain one or more inferences or other output values, classifications, or predictions, or for at least one embodiment, input data can be received by interface layer 508 and directed to inference module 518, although a different system or service can be used as well. In at least one embodiment, inference module 518 can obtain an appropriate trained network, such as a trained deep neural network (DNN) as discussed herein, from model repository 516 if not already stored locally to inference module 518. Inference module 518 can provide data as input to a trained network, which can then generate one or more inferences as output. This may include, for example, a classification of an instance of input data. In at least one embodiment, inferences can then be transmitted to client device 502 for display or other communication to a user. In at least one embodiment, context data for a user may also be stored to a user context data repository 522, which may include data about a user which may be useful as input to a network in generating inferences, or determining data to return to a user after obtaining instances. In at least one embodiment, relevant data, which may include at least some of input or inference data, may also be stored to a local database 534 for processing future requests. In at least one embodiment, a user can use account information or other information to access resources or functionality of a provider environment. In at least one embodiment, if permitted and available, user data may also be collected and used to further train models, in order to provide more accurate inferences for future requests. In at least one embodiment, requests may be received through a user interface to a machine learning application 526 executing on client device 502, and results displayed through a same interface. A client device can include resources such as a processor 528 and memory 562 for generating a request and processing results or a response, as well as at least one data storage element 552 for storing data for machine learning application 526.

In at least one embodiment a processor 528 (or a processor of training module 512 or inference module 518) will be a central processing unit (CPU). As mentioned, however, resources in such environments can utilize GPUs to process data for at least certain types of requests. With thousands of cores, GPUs, such as PPU 300 are designed to handle substantial parallel workloads and, therefore, have become popular in deep learning for training neural networks and generating predictions. While use of GPUs for offline builds has enabled faster training of larger and more complex models, generating predictions offline implies that either request-time input features cannot be used or predictions must be generated for all permutations of features and stored in a lookup table to serve real-time requests. If a deep learning framework supports a CPU-mode and a model is small and simple enough to perform a feed-forward on a CPU with a reasonable latency, then a service on a CPU instance could host a model. In this case, training can be done offline on a GPU and inference done in real-time on a CPU. If a CPU approach is not viable, then a service can run on a GPU instance. Because GPUs have different performance and cost characteristics than CPUs, however, running a service that offloads a runtime algorithm to a GPU can require it to be designed differently from a CPU based service.

In at least one embodiment, video data can be provided from client device 502 for enhancement in provider environment 506. In at least one embodiment, video data can be processed for enhancement on client device 502. In at least one embodiment, video data may be streamed from a third party content provider 524 and enhanced by third party content provider 524, provider environment 506, or client device 502. In at least one embodiment, video data can be provided from client device 502 for use as training data in provider environment 506.

In at least one embodiment, supervised and/or unsupervised training can be performed by the client device 502 and/or the provider environment 506. In at least one embodiment, a set of training data 514 (e.g., classified or labeled data) is provided as input to function as training data. In an embodiment, the set of training data may be used in a generative adversarial training configuration to train a generator neural network.

In at least one embodiment, training data can include images of at least one human subject, avatar, or character for which a neural network is to be trained. In at least one embodiment, training data can include instances of at least one type of object for which a neural network is to be trained, as well as information that identifies that type of object. In at least one embodiment, training data might include a set of images that each includes a representation of a type of object, where each image also includes, or is associated with, a label, metadata, classification, or other piece of information identifying a type of object represented in a respective image. Various other types of data may be used as training data as well, as may include text data, audio data, video data, and so on. In at least one embodiment, training data 514 is provided as training input to a training module 512. In at least one embodiment, training module 512 can be a system or service that includes hardware and software, such as one or more computing devices executing a training application, for training a neural network (or other model or algorithm, etc.). In at least one embodiment, training module 512 receives an instruction or request indicating a type of model to be used for training, in at least one embodiment, a model can be any appropriate statistical model, network, or algorithm useful for such purposes, as may include an artificial neural network, deep learning algorithm, learning classifier, Bayesian network, and so on. In at least one embodiment, training module 512 can select an initial model, or other untrained model, from an appropriate repository 516 and utilize training data 514 to train a model, thereby generating a trained model (e.g., trained deep neural network) that can be used to classify similar types of data, or generate other such inferences. In at least one embodiment where training data is not used, an appropriate initial model can still be selected for training on input data per training module 512.

In at least one embodiment, a model can be trained in a number of different ways, as may depend in part upon a type of model selected. In at least one embodiment, a machine learning algorithm can be provided with a set of training data, where a model is a model artifact created by a training process. In at least one embodiment, each instance of training data contains a correct answer (e.g., classification), which can be referred to as a target or target attribute. In at least one embodiment, a learning algorithm finds patterns in training data that map input data attributes to a target, an answer to be predicted, and a machine learning model is output that captures these patterns. In at least one embodiment, a machine learning model can then be used to obtain predictions on new data for which a target is not specified.

In at least one embodiment, training and inference manager 532 can select from a set of machine learning models including binary classification, multiclass classification, generative, and regression models. In at least one embodiment, a type of model to be used can depend at least in part upon a type of target to be predicted.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A method for determining, using a machine learning framework, a candidate molecule for satisfying a design criteria, the method comprising:
   receiving an input molecule data structure and the design criteria;
   selecting, based on the input molecule data structure and the design criteria, a plurality of exemplary molecule data structures from a database;
   providing the input molecule data structure as input to a trained encoder of the machine learning framework and processing, by the trained encoder, the input molecule data structure to generate an embedding of the input molecule data structure, wherein the embedding of the input molecule data structure is a numerical vector or tensor of a pre-defined dimension;
   providing the plurality of exemplary molecule data structures as input to the trained encoder and processing by the trained encoder, the plurality of exemplary molecule data structures to generate embeddings of the plurality of exemplary molecule data structures, wherein each respective embedding of a respective exemplary molecule data structure is a numerical vector or tensor of a pre-defined dimension;
   fusing, by a trained cross-attention mechanism, the embedding of the input molecule data structure and the embeddings of the exemplary molecule data structures to generate a fused embedding; and
   providing the fused embedding as input to a trained decoder of the machine learning framework and processing, by the trained decoder, the fused embedding to generate a candidate molecule data structure.

2. The method of claim 1, wherein the encoder comprises a bidirectional encoder and the decoder comprises an autoregressive decoder.

3. The method of claim 2, wherein the encoder and decoder are trained using a ZINC dataset.

4. The method of claim 1, wherein the input molecule data structure and the plurality of exemplary molecule data structures are simplified molecular-input line-entry system (SMILES) string data structures.

5. The method of claim 1, wherein the pre-trained cross-attention mechanism is trained in accordance with an objective to predict a nearest neighbor of the input molecule data structure in a training data set stored in the database, given as:

$$\mathcal{L}(\theta) = \Sigma_{i=1}^{B} CE(DEC(f_{CA}(e_{in}^{(i)}, E_r^{(i)}; \theta)), x_{1NN}^{(i)}).$$

6. The method of claim 1, wherein the selecting, based on the input molecule data structure and the design criteria, the plurality of exemplary molecule data structures from the database comprises:
   calculating, in accordance with a score function, a score value for each of a plurality of molecule data structures stored in the database; and
   selecting, via a retriever of the machine learning framework, K molecule data structures from the database as the plurality of exemplary molecule data structures, wherein the K exemplary molecule data structures are the K molecule data structures in the database having the top score values.

7. The method of claim 6, wherein the design criteria specifies L properties for the candidate molecule, and wherein each molecule stored in the database has at least one predicted property value of L properties that is greater than a threshold value.

8. The method of claim 1, wherein the encoder, the decoder, and the cross-attention mechanism comprise instructions configured to be executed by one or more processors of a computer device.

9. The method of claim 1, further comprising:
   generating, based on the fused embedding, a plurality of perturbed embeddings by adding noise to the fused embedding;
   providing each perturbed embedding in of the plurality of perturbed embeddings to the trained decoder and processing, by the trained decoder, the plurality of perturbed embeddings to generate a plurality of second candidate molecule data structures;
   calculating a score value for each second candidate molecule data structure of the plurality of second candidate molecule data structures; and
   selecting a respective second candidate molecule data structure with the highest score value of the score values calculated for the second candidate molecule data structures as a best candidate molecule data structure.

10. The method of claim 9, further comprising:
    calculating a score value for the input molecule data structure;
    comparing the score value for the input molecule data structure with the score value for the best candidate molecule data structure;

in response to determining that the score value for the best candidate molecule data structure is greater than the score value for the input molecule data structure, updating the database by adding the best candidate molecule data structure to the database; and repeating the method for a new input molecule using the updated database.

11. The method of claim 1, wherein providing the input molecule data structure and generating the embedding of the input molecule data structure is performed by a first instance of the trained encoder, wherein the providing the plurality of exemplary molecule data structures as input to the trained encoder and generating the embeddings of the plurality of exemplary molecule data structures is performed via a plurality of second instances of the trained encoder, and wherein the first instance of the trained encoder and the plurality of second instances of the trained encoder generate the embedding of the input molecule data structure and the embeddings of the plurality of exemplary molecule data structures in parallel.

12. The method of claim 1, wherein (i) the providing the input molecule data structure as input to the trained encoder and generating the embedding of the input molecule data structure and (ii) the providing the plurality of exemplary molecule data structures as input to the trained encoder and generating the embeddings of the plurality of exemplary molecule data structures are performed sequentially using a single instance of the trained encoder.

13. A system for determining, using a machine learning framework, a candidate molecule for satisfying a design criteria, the system comprising:

a memory storing a database containing a plurality of molecule data structures; and at least one processor, communicatively coupled to the memory, and the at least one processor being configured to:

receive an input molecule data structure and the design criteria;

select, based on the input molecule data structure and the design criteria, a plurality of exemplary molecule data structures from the database;

provide the input molecule data structure as input to a trained encoder of the machine learning framework and process, via the trained encoder, the input molecule data structure to generate an embedding of the input molecule data structure, wherein the embedding of the input molecule data structure is a numerical vector or tensor of a pre-defined dimension;

provide the plurality of exemplary molecule data structures as input to the trained encoder and process via the trained encoder, the plurality of exemplary molecule data structures to generate embeddings of the plurality of exemplary molecule data structures, wherein each respective embedding of a respective exemplary molecule data structure is a numerical vector or tensor of a pre-defined dimension;

fuse, via a trained cross-attention mechanism, the embedding of the input molecule data structure and the embeddings of the exemplary molecule data structures to generate a fused embedding; and provide the fused embedding as input to a trained decoder of the machine learning framework and process, via the trained decoder, the fused embedding to generate a candidate molecule data structure.

14. The system of claim 13, wherein the encoder comprises a bidirectional encoder and the decoder is comprises an autoregressive decoder.

15. The system of claim 13, wherein the input molecule data structure and the plurality of exemplary molecule data structures are simplified molecular-input line-entry system (SMILES) string data structures.

16. The system of claim 13, wherein the at least one processor is configured to select, based on the input molecule data structure and the design criteria, the plurality of exemplary molecule data structures from the database by:

calculating, in accordance with a score function, a score value for each of a plurality of molecule data structures stored in the database; and selecting, via a retriever of the machine learning framework, K molecule data structures from the database as the number of exemplary molecules, wherein the K exemplary molecules are the K molecules in the database having the top score values.

17. The system of claim 13, wherein the at least one processor is further configured to:

generate, based on the fused embedding, a plurality of perturbed embeddings by adding noise to the fused embedding;

provide each perturbed embedding of the plurality of perturbed embeddings to the trained decoder and process, via the trained decoder, the plurality of perturbed embeddings, to generate a plurality of second candidate molecule data structures;

calculate a score value for each second candidate molecule data structure of the plurality of second candidate molecule data structures; and select a respective second candidate molecule data structure with the highest calculated score value of the score values calculated for the second candidate molecule data structures as a best candidate molecule data structure.

18. The system of claim 17, wherein the at least one processor is further configured to:

calculate a score value for the input molecule data structure;

compare the score value for the input molecule data structure with the score value for the best candidate molecule data structure;

in response to determining that the score value for the best candidate molecule data structure is greater than the score value for the input molecule data structure, update the database by adding of the best candidate molecule data structure to the database; and repeat the method for a new input molecule using the updated database.

19. A non-transitory computer readable medium storing instructions that, in response to being executed by a computing device, cause the computing device to:

select, based on an input molecule data structure and a design criteria, a plurality of exemplary molecule data structures from a database;

provide the input molecule data structure as input to a trained encoder of the machine learning framework and process, by the trained encoder, the input molecule data structure to generate an embedding of the input molecule data structure, wherein the embedding of the input molecule data structure is a numerical vector or tensor of a pre-defined dimension:

provide the plurality of exemplary molecule data structures as input to the trained encoder and process, by the trained encoder, the plurality of exemplary molecule data structures to generate embeddings of the plurality of exemplary molecule data structures, wherein each respective embedding of a respective exemplary molecule data structure is a numerical vector or tensor of a pre-defined dimension;

fuse, via a trained cross-attention mechanism, the embedding of the input molecule data structure and the embeddings of the exemplary molecule data structures to generate a fused embedding; and provide the fused embedding as input to a trained decoder of the machine learning framework and process, via the trained decoder, the fused embedding to generate a candidate molecule data structure.

* * * * *